(12) United States Patent
Nilsen

(10) Patent No.: US 8,158,443 B2
(45) Date of Patent: Apr. 17, 2012

(54) TURBIDIMETRIC IMMUNOASSAY FOR ASSESSING HUMAN CYSTATIN C

(75) Inventor: Tom Nilsen, Moss (NO)

(73) Assignee: Gentian AS, Moss (NO)

( * ) Notice: Subject to any disclaimer, the term of this patent is extended or adjusted under 35 U.S.C. 154(b) by 0 days.

(21) Appl. No.: 12/598,058

(22) PCT Filed: May 19, 2008

(86) PCT No.: PCT/EP2008/056134
§ 371 (c)(1),
(2), (4) Date: Oct. 7, 2010

(87) PCT Pub. No.: WO2008/142057
PCT Pub. Date: Nov. 27, 2008

(65) Prior Publication Data
US 2011/0033950 A1     Feb. 10, 2011

(30) Foreign Application Priority Data

May 21, 2007  (EP) .................................. 07010086

(51) Int. Cl.
*G01N 33/543* (2006.01)
(52) U.S. Cl. ....... 436/518; 435/7.1; 435/7.92; 435/7.93; 435/7.94; 436/501
(58) Field of Classification Search .................. None
See application file for complete search history.

(56) References Cited

U.S. PATENT DOCUMENTS

| | | | |
|---|---|---|---|
| 4,210,723 A | 7/1980 | Dorman et al. | |
| 4,351,824 A | 9/1982 | Lehrer | |
| 5,571,728 A * | 11/1996 | Kraus | 436/534 |
| 6,200,820 B1 * | 3/2001 | Hansen et al. | 436/523 |
| 6,248,597 B1 | 6/2001 | Eda et al. | |
| 6,436,389 B1 * | 8/2002 | Gage et al. | 424/85.1 |
| 6,828,158 B2 | 12/2004 | Eda et al. | |
| 2001/0026927 A1 * | 10/2001 | Yokohama et al. | 435/7.92 |
| 2001/0026945 A1 | 10/2001 | Eda et al. | |

FOREIGN PATENT DOCUMENTS

| | | |
|---|---|---|
| EP | 0898169 A2 | 2/1999 |
| WO | WO-2007/102054 A2 | 9/2007 |

OTHER PUBLICATIONS

Newman et al., Serum cystatin C measured by automated immunoassay: A more sensitive marker of changes in GFR than serum creatinine, Kidney International, vol. 47, 1995, pp. 312-318.*
Ishiguro et al., The use of monoclonal antibodies to define levels of cystatin c in normal human serum, Hybridoma, vol. 8, No. 3, 1989, pp. 303-313.*
Tan et al., Diabetes Care 2002, 252004-2009.
Sun et al., Nephrol. Dial. Transplant. 2010, 25, 1489-1496.
Chew et al., Clin. Biochem. Rev. 2008, 2, 47-62.
Larsson et al., Poultry Sci. 1993, 72, 1807-1812.
Carlander et al., Upsala J. Med. Sci. 2001, 106, 189-195.
Horton et al., J. Inv. Dermatol. 1985, 86, 96-99.
Newman David J et al: "Serum cystatin C measured by automated immunoassay: A more sensitive marker of changes in GFR than serum creatinine" Kidney International, vol. 47, No. 1, 1995, pp. 312-318.
Kyhse-Andersen Jan et al: "Serum cystatin C, determined by a rapid, automated particle-enhanced turbidimetric method, is a better marker than serum creatinine for glomerular filtration rate", Clinical Chemistry, vol. 40, No. 10, 1994, pp. 1921-1926.
Finney Hazel et al: "Initial evaluation of cystatin C measurement by particle-enhanced immunonephelometry on the Behring nephelometer systems (BNA, BN II)" Clinical Chemistry, vol. 43, No. 6 Part 1, 1997, pp. 1016-1022.
Sunde Kathrin et al: "Performance characteristics of a cystatin C immunoassay with avian antibodies" UPSALA Journal of Medical Sciences 2007, vol. 112, No. 1, Mar. 2, 2007, pp. 21-37.
Flodin M et al: "Evaluation of Gentian cystatin C reagent on Abbott Ci8200 and calculation of glomerular filtration rate expressed in mL/min/1.73 m(2) from the cystatin C values in mg/L", Scandinavian Journal of Clinical and Laboratory Investigation 2007, vol. 67, No. 5, Feb. 15, 2007 pp. 560-567.
Lewis A V et al: "Improved immunoturbidimetric assay for cystatin C", Annals of Clinical Biochemistry, vol. 38, No. 2, Mar. 2001, pp. 111-114.
PCT/ISA/210 (ISR) Issued in PCT/EP2008/056134, Jul. 7, 2008, Gentian AS.
PCT/ISA/237 (Written Opinion) Issued in PCT/EP2008/056134, Jul. 7, 2008, Gentian AS.
Abrahamson, M. et al. "Isolation of Six Cysteine Proteinase Inhibitors from Human Urine" The Journal of Biological Chemistry 261(4): 11282-11289 (1986).
Abrahamson, M. et al.., "Structure Expression of the Human Cystatin C Gene" Biochem. J. 268: 287-294 (1990). Coll, E. et al. "Serum Cystatin C as a New Marker for Noninvasive Estimation of Glomerular Filtration Rate and as a Marker for Early Renal Impairment" American Journal of Kidney Diseases 36(1): 29-34 (2000).
Grubb, A. et al. "Human γ-Trace, A Basic Microprotein: Amino Acid Sequence and Presence in the Adenohypophysis" Proc. Natl. Acad. Sci. USA 79: 3024-3027 (1982).
Grubb, A. et al. "Simple Cystatin C-Based Prediction Equations . . . " Clinical Chemistry 51(8): 1420-1431 (2005).
Heymsfield, S. et al. "Measurement of Muscle Mass in Humans: Validityu of the 24-Hour Urinary Creatinine Method" The American Journal of Clinical Nutrition 37: 478-494 (1983).
Jacobsson, B. et al. "Transthyretin and Cystatin C are Catabolized in Proxmimal Tubular Epithelial Cells and the Proteins are not Useful . . . " Histopathology 26: 559-564 (1995).

(Continued)

*Primary Examiner* — Bao Thuy L Nguyen
*Assistant Examiner* — Gary W Counts
(74) *Attorney, Agent, or Firm* — Edwards Wildman Palmer LLP; Peter C. Lauro, Esq.; Weiying Yang, Esq.

(57) ABSTRACT

There is a demand for improved turbidimetric immunoassays for human Cystatin C in biological samples, especially in human clinical samples of body fluids. The present invention provides a turbidimetric immunoassay method and reagent set enabling measurement of human Cystatin C by turbidimetric methods, resulting in a surprisingly stronger and faster turbidimetric signal than in the present state of the art. The increased and faster signal is accomplished by the use of new reagents and compositions, and enables shorter assay times and kinetic reading with a stronger signal, improving overall assay speed and quality. Improved robustness to lipid interference and improved linearity is achieved.

20 Claims, 3 Drawing Sheets

OTHER PUBLICATIONS

Mussap, M. et al. "Quantitative Automated Particle-Enhanced Immunoephelomertric Assay for the Routinary Measurement of Human Cystatin C" Clinical Chemistry and Laboratory Medicine, 36(11): 859-865 (1998).

Newman, D.J. et al. Turbidity in Innumoturbidimetric Assay Ann. Clin. Biochem. 27: 509(1990), Letters to the Editor, including Dhar et al. reply to Newman et al.

Perrone, R. D. et al. "Serum Creatinine as an Index of Renal Function: New Insights into Old Concepts" Clin. Chem. 38(10: 1933-1953 (1992).

Shemesh, O. et al. "Limitations of Creatinine As a Filtration Marker in Glomerulopathic Patients" Kidney Journal 28: 830-838(1985).

Stowe, H. et al. "Analytical Performance of a Particle-Enhanced Nephelometric Immunoassay for Serum Cystatin C Using Rate Analysis" Clinical Chemistry 47(8): 1482-1485 (2001).

Tanaka, et al. "A Sol Particle Homogeneous Immunoassay for Measuring Serum Cytostatin C Clinical" *Biochemistry* 37: 27-35 (2007).

Larsson, A., Anti-Cystatin C Antiserum Investigation Protocol and Report, *Anti-Cystatin C Antiserum Investigation Protocol*, dated Jun. 24, 2009, pp. 1-7.

Butch, A.W., Dilution Protocols for Detection of Hook Effects/ Prozone Phenomenon, *Clinical Chemistry*, 2000, 46 (10), 1719-1720.

* cited by examiner

TURBIDIMETRIC IMMUNOASSAY FOR ASSESSING HUMAN CYSTATIN C

RELATED APPLICATION

This application is the U.S. national phase, pursuant to 35 U.S.C. §371, of PCT international application Ser. No. PCT/EP2008/056134, filed May 19, 2008, designating the United States and published in English on Nov. 27, 2008 as publication WO 2008/142057 A1, which claims priority to European application Ser. No. 07010086.2, filed May 21, 2007. The entire contents of the aforementioned patent applications are incorporated herein by this reference.

The present invention relates to an improved turbidimetric immunoassay for assessing human Cystatin C in a human body liquid sample by making use of specific nanoparticle-antibody conjugates and measuring conditions; a method for the assessment of the glomerular filtration rate of a patient by making use of said assay; corresponding reaction kits; and the use of improved nanoparticle-antibody conjugates for the above mentioned medical purpose.

BACKGROUND OF THE INVENTION

Cystatin C was discovered and characterized in 1981 by A. Grubb and H. Lovberg [Grubb A O, et al: *Proc. Nati. Acad. Sci. USA* 1982;79]. Cystatin C was the first protein discovered in what later has been named the Cystatin protein superfamily. The Cystatin protein superfamily is a group of proteins that inhibits of cystein protease enzymes. Other biological functions of Cystatin C are presently under investigation. Contrary to other members of the Cystatin superfamily, Cystatin C is present in all body fluids, while the total composition of different Cystatins varies from body fluid to body fluid, and in different compartments [Abrahamson M, et al: *J. Biol. Chem.* 1986; 261:11282]. In 1990, Abrahamsson et al. demonstrated that Cystatin C is produced at a stable rate and by all (or close to all) nucleated cells in the human body, being what is called a "householding" protein [Abrahamson M, et al: *Biochem. J.* 1990; 268:287-94].

Cystatin C—with a molecular mass of 13 kD—is freely filtered through the normal glomerular membrane of the kidney, but is then reabsorbed and catabolized in the "proximal tubuli", the compartment of the kidneys that re-absorbs most of the peptides and smaller proteins that pass the glomerular membrane. In this way the kidneys preserve these proteinaceous materials for the body and hinder loss to the urine (Jacobsson B, et al: *Histopathology* 1995; 26:559-64.) [Heyms S B, et al: *Am. J. Clin. Nutr.* 1983; 37: 478].

Creatinine, until now the mostly used marker for glomerular filtration rate (GFR), is a small molecular weight molecule produced in muscles cell. The rate of formation and secretion of creatinine is therefore closely linked to the muscular mass of the body. It is well known that the muscular mass of an individual in a population varies considerably.

Elderly people often have a low muscular mass compared to the body mass, also many patients lose muscular mass as their diseases progress. Children generally have a different relative muscular mass compared to adults, and men have in average a higher relative muscular mass than women. Therefore, when serum creatinine concentration is used as a marker for glomerular filtration rate, the serum creatinine value can be found within the reference range even when a 50% reduction in glomerular filtration rate has taken place [Shemesh O, et al: *Kidn. Int.* 1985; 28: 830-8]. Also diet influences the serum level of creatinine significantly, especially a protein rich diet [Perrone R D, et al: *Clin. Chem.* 1992; 38: 1933-53].

Serum and plasma creatinine measurements are not reliable, "gold standard methods" for measurement of glomerular filtration rate. The use of intravenous injections of radio labeled substances like Cr-51-EDTA or Tc-99m-DTPA, or injections of iodinated agents like iohexol, have therefore gained some popularity. These methods are expensive, time-consuming and injections are necessary—and often repeated blood sampling. In the publication "Simple Cystatin C-Based Prediction Equations for Glomerular Filtration Rate Compared with the Modification of Diet in Renal Disease Prediction Equation for Adults and the Scwartz and the Counahan-Barratt Prediction Equations for Children", by Grubb & al. in Clinical Chemistry 51:8, 1420-1431, it was demonstrated that simple Cystatin C measurements in blood can replace complicated methods of measuring the glomerular filtration rate.

Cystatin C measurement originally used classical biochemical methods, but soon moved over to turbidimetric and nephelometric immunoassays. The Dade-Behring Company pioneered nephelometric measurement methods. See also CoII, E & al. Am. J. Kidney Disease 2000; 36, 2934. The nephelometric methods are very reliable. The disadvantage of nephelometric methods is that the instruments themselves have rather slow processing speed compared to automated spectrophotometers based on light transmission. Nephelometers produced by Dade Behring, typically the BNII nephelometer and ProSpec nephelometers, and Beckman Instruments, have gained substantial market penetration, but are much less widespread than instruments based on transmission measurements. Nephelometers also have a much lower sample throughput than the large automated instruments based on transmission measurements.

H. Stone & al. in the article "Analytical performance of a particle-enhanced nephelometric immunoassay for serum Cystatin C using rate analysis", in Clinical Chemistry Vol 8, pp 1482-85, 2001, presented a rate nephelometric method. However, nephelometric instruments have limited capacity for a large number of samples, and the number of nephelometric instruments is limited. Therefore there was a demand to move to absorption spectrophotometric-homogeneous instruments, since such instruments are more abundant and have a higher capacity.

Dako Cytomation, Denmark, has pioneered the field of turbidimetric Cystatin C immunoassays. The state of the art is described in the following articles: "Cystatin C—The marker of choice for renal function testing" by C. Schmidt in European Clinical Laboratory, 10 Feb. 2004. "New improved automated particle enhanced turbidimetric immunoassay for quantitative determination of human Cystatin C in serum and plasma" by C. Schmidt, C. Kjøller and K Grønkjær, a presentation downloaded from the Dako Cytomation AS' web site July 2005 (incorporated by reference).

Turbidimetric measurements are—however—disturbed by turbidity in samples, as described in the article "Turbidity in immunoturbidimetric assays" by Dahr & al, in Ann. Clin. Biochem. Vol 27, p. 509, 1990. At the 29th Nordic Congress of Clinical Chemistry, Malmo, Sweden, 24-27 Apr., 2004, A. Grubb presented results on interference from triglycerides in serum and plasma samples on the results from Cystatin C measurements. There is therefore still a need for improvements on the turbidimetric immunoassay for human Cystatin C.

An alternative to homogeneous immunoassay systems would be a separation-based non-homogeneous immunoassay systems. The advantage of non-homogeneous immunoassay systems is characterized by a separation step with washing during the performance of the assay. The advantage of these systems is that they—by means of the washing—remove any interfering substances. Furthermore, it allows washing away non-bound antibodies and non-bound enzymes or fluorescent or colored or other signal-giving moieties. These methods are generally non-competitive since the substance to be measured—hereinafter called the analyte—does not have to compete with labeled analogues for the binding to the antibodies. This aspect, and the use of washing steps, makes it possible to use immobilized antibodies and labeled antibodies in excess, rendering a high sensitivity and usually a high level of accuracy, especially if high quality antibodies are used.

There are numerous textbooks on solid phase and other non-homogeneous immunoassay systems. Big automated systems are commercially available. Abbott Diagnostic Division, US, sells reagents for ImX, AxSYM and other automated non-homogeneous immunoassay instruments; Roche Diagnostics, Germany, sells reagents for Elecsys and other non-homogeneous immunoassay systems; and there are numerous other suppliers of non-homogeneous immunoassay systems and reagents. A still very popular non-homogeneous immunoassay system is the so-called microtitre immunoassay systems. These systems are slow but reliable and inexpensive. The general immunoassay literature gives a lot of information on these systems, which are well known to those skilled in the art.

The disadvantage of non-homogeneous immunoassay systems is the lack of capacity for a high number of assays per time unit, i.e. per hour running time. The methods involve separation and washing steps, which—although automated—occupy instrument-running time. Furthermore, since solid phases are involved, special devices or solid phases are often used, which have a certain production price, even when mass-produced. High through-put and speed of result generation have become more and more important in recent years, due to the ever increasing number of tests to run. There is a demand to move assays from non-homogeneous, often solid phase based, immunoassay technologies, to homogeneous immunoassay systems.

Homogeneous immunoassay systems are simple in construction and have a higher throughput capacity. The reagents are mixed, incubated and measured, either during or after incubation. Endpoint signals or differences in signal between different time points or continuous kinetic measurements are used. Signals may be measurements of fluorescence, color or opacity (turbidimetry). In particular, large automated instruments for measurements of color and/or opacity/turbidimetry have been very successful. The Hitachi Company in Japan pioneered this large-scale automation, working together with Roche, but also numerous other manufacturers including Olympus and Bayer supply such instruments and reagents. These instruments are automated multi-well spectrophotometers measuring transmission of light through a mixture of the sample and reagents at different wavelengths and at different time points. Since the turbidimetric Cystatin C immunoassays run on such homogeneous high capacity instruments, this is another reason why high quality turbidimetric Cystatin C assays are in demand.

Most homogeneous immunoassay systems are based on mixing the sample with reagent solutions comprising a well-controlled concentration of labeled analyte or analyte analogue, and antibodies having specific affinity for the analyte. The analyte molecules in the sample compete with the labeled analyte or analyte analogue, and a signal is generated. The vast immunoassay literature teaches the use of different labels and analogues. Here it should be noted that—so far—there has been limited success using homogeneous immunoassay methods for high molecular weight analytes (molecular mass above 4000) generating colored signals. (There has been success using fluorescent techniques, e.g. proximity assays, but there are not many high throughput automated fluorometers available, and therefore these technologies do not serve the purpose of the present invention). The EMIT technology from Syva and the CDEIA technology from Microgenics, both companies located in California, have been successful with color signals in homogeneous immunoassays for low molecular mass analytes. For high molecular mass analytes, particle enhanced turbidimetric measurements have been the most successful technology for the automated multi-well spectrophotometers measuring transmission of light through the mixture of the sample and the reagents. Turbidimetric methods are therefore preferred for higher molecular weight analytes. General descriptions of turbidimetric methods are found in numerous immunoassay textbooks.

Why are high precision measurements of Cystatin C necessary? From the perspective of biology, the literature on the biology of Cystatin C and creatinine, as well as the meta-analysis cited above, point in the direction of the use of Cystatin C instead of creatinine to monitor and diagnose reduced glomerular filtration rate. However, although the biological argument is in favor of using Cystatin C, the biological advantage is only of importance if the accuracy and precision of the Cystatin C analysis is good. The accuracy and precision of creatinine measurements is excellent, and the medical advantage of analyzing Cystatin C instead of creatinine is easily lost if the accuracy or precision of the Cystatin C immunoassay methods is too low.

Newman & al, Kidney Int. Vol 47 (1995), pp 312-318, teach an optimized assay using 77 nm (before coating) particles covalently coupled to rabbit anti-human Cystatin C immunoglobulin fraction. They do not teach the use of affinity purified antibodies, and they say nothing about the concentration of binding antibodies in the immunoglobulin fraction they use. They teach from 5 to 30% antibody weight per particle weight, optimized at 5%, however say nothing about the fraction of antibodies having affinity for Cystatin C in the immunoglobulin fraction. Typically, a good conventional antiserum comprises 5 to 15% active antibodies of the total antibodies in immunoglobulin fraction, which would imply 0.25 to 0.75 wt.-% of active antibodies per weight of particles. This is very low, that is probably the reason why Newman et al had to go all the way down to 340 nm to obtain a good signal. This is also why they observed a background signal being very high. Newman et al state in Table 1 that the particles are diluted down (how much is not stated) to give a starting absorbance of 0.7 at 0.74 cm light path length, which is still very high (more than an absorbance of 0.9 at 1 cm light path length, which is most often used), and therefore will lead to a very high background in the assay. This is maybe the main reason why the method of Newman et al never was commercialized or taken into clinical use, and it teaches away from using low wavelengths in Cystatin C particle enhanced turbidimetric immunoassay. All commercial products for turbidimetric measurements of Cystatin C on the market therefore use wavelengths above 500 nm.

A problem to be solved by the present invention is to provide an immuno-turbidimetric Cystatin C immunoassay with improved accuracy and/or precision and/or less interference from lipids and hemoglobin in test sample if compared to corresponding commercially available turbidimetric assays.

Another drawback of the prior art of turbidimetric measurements of Cystatin C is the low rate of change in turbidimetry, which leads to long assay time and/or high imprecision.

A further problem to be solved by the present invention is therefore, to provide a faster turbidimetric measurements of Cystatin C.

SUMMARY OF THE INVENTION

Figure 1:
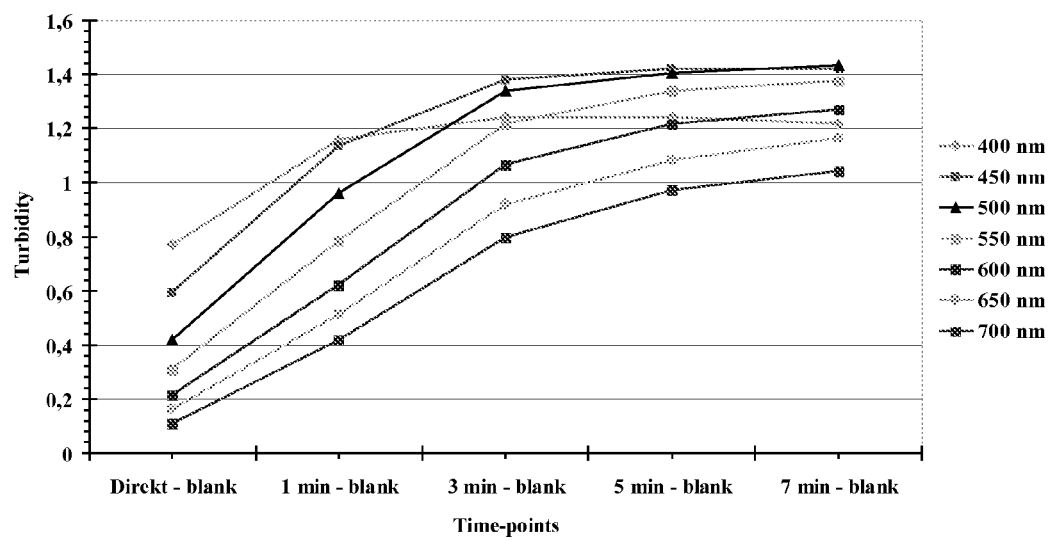
FIG. 1 shows the change of turbidity/absorbance for different wavelength values at different time points after the addition of the immunoparticles to the reaction mixture, using an Hitachi 917 instrument from Roche Diagnostics for measurements. The steepest initial absorbance increase is observed at 450 nm.

The above problems associated with the prior art turbidimetric immunoassays for the measurement of Cystatin C could, surprisingly, be solved by a turbidimetric method as defined in the claims and explained in more detail in the subsequent parts of the description. Said method of the invention particularly makes use of improved nanoparticle-immunoconjugates in combination with specific measuring conditions which allow a more rapid and/or more sensitive and/or more reliable Cystatin C measurement under different experimental conditions, as in particular, different Cystatin C concentrations, different measuring wavelengths, different reaction times and different temperatures. Further advantages of the invention are evident form the attached experiments.

By careful adjustments of immunoparticles, measuring conditions and optionally assay reagents, a surprisingly stronger and faster turbidimetric signal could be observed, and thereby interferences could be reduced and the linearity could be improved without loosing accuracy. Also the assay time could be reduced.

Best modes of the invention will be described below, but also other reagents and sequences of steps and times as used for preparing the reaction mixture and for performing the measurement can be used to achieve this surprising result.

There are several suppliers of nanoparticles, e.g. Bangs Laboratories Inc, USA and Merck S.A., France. Numerous suppliers of conjugation services for coupling of antibodies to nanoparticles can be found on the Internet. Dako Cytomation AS, Denmark, supplies nanoparticles conjugated to anti-Cystatin C antibodies, and they were tested by the present inventors, whether or not to achieve the objective of this invention. However said prior art products turned out to be unsuccessful.

The present inventors observed that, i.a., the particle size must be balanced carefully. Large particles create a good signal, however the background is high, and the binding capacity is low, so that a lot of particles must be added, creating even higher background turbidity. Previous suppliers of assays, like Dako Cytomation AS, product numbers LX002/EFG/CS/25.10.04, S2361/EFG/KGR/09.07.03 and X0974/EFG/SUM/09.09.04, have not achieved good turbidimetric signals.

In addition, it was unexpectedly observed that surprisingly high net changes in absorbance can be observed at detection wavelengths below 500 nm and above 340 nm, i.e. in a wavelength range not suggested by the prior art.

Definitions of General Terms

A "body liquid sample" as used in the assay method according to the invention is a sample derived from a mammal, in particular a human being, and which contains Cystatin C, in particular human Cystatin C. Any Cystatin C containing liquid sample may be used. Said samples to be assayed according to the invention may be any Cystatin C containing biological fluid or tissue extract and may be pre-treated prior to the assay. Examples of suitable samples are blood, blood fractions, like serum and plasma, and pre-treated blood, like EDTA-blood, or EDTA-plasma, citrate-plasma, heparin plasma, or urine samples. The originally obtained samples or fractions thereof may be further modified by methods known in the art, as for example by fractionation or dilution. Fractionation may be performed to remove constituents which might disturb the assay. Dilution may be performed by mixing the original sample or fraction with a suitable sample liquid, like a suitable buffer, in order to adjust the concentration the constituents, as for example of the analyte. Such modified samples exemplify samples "derived from" the original body fluid sample collected or isolated from the body of the mammal.

An "analyte" to be assayed according to the invention is Cystatin C, in particular human Cystatin C, as formed by the body of a healthy or diseased individual. Although not necessary, it may also be possible to use as the analyte a derivative of Cystatin C or a mixture of natural Cystatin C and Cystatin C derivative(s). Non-limiting examples of Cystatin C derivatives are Cystatin C compounds carrying a suitable detectable marker, as for example a radioactive, metal or chromophor label.

"Assessing" or "assessment" is intended to include both quantitative and qualitative determination in the sense of obtaining an absolute value for the amount or concentration of the analyte, here Cystatin C, present in the sample, and also obtaining an index, ratio, percentage, visual or other value indicative of the level of analyte in the sample. Assessment may be direct or indirect and the chemical species actually detected need not of course be the analyte itself but may for example be a derivative thereof.

"Homogeneous immunoassays" are, as opposed to non-homogeneous immunoassays, simpler in construction and have a higher throughput capacity. In particular, homogeneous assays do not encompass a pre-treatment step of the sample in the form of separation step, for example by applying the sample on a solid matrix, like a chromatography column a plastic filter, plastic surfaces in tubes, wells or on beads, washing the matrix during the assay and separating the analyte from parts of the original constituents of the original complex sample, which procedures result in long assay times and in a low capacity of the multianalyzer instruments in the case of a non-homogeneous assay. For a homogeneous assay the sample and reagents are mixed, incubated and measured, either during or after incubation. Endpoint signals or differences in signal between different time points or continuous kinetic measurements are used.

A "particle enhanced" turbidimetric measurements or immunoassay is based on the "light scattering properties" associated with the nanoparticles or nanoparticle-immunoconjugates as used according to the invention. Such nanoparticles are usually approximately spherical, preferably with a narrow size distribution. The size of said particles is normally expressed via their mean diameter. According to the well-known laws of light scattering said light scattering properties may be influenced by the particle size, and/or the ratio of the refractive index of the particle to that of the medium. Weak light scattering properties may result from a small particle size, and/or a low ratio of the refractive index of the particle to that of the medium (see also Rayleigh's law of light scattering)

The size and/or the refractive index ratio of the nanoparticles are such that they can cause light scattering at the wavelength used for detection of agglutinated nanoparticle-immunoconjugates. That size is generally chosen to be smaller than that detection wavelength.

The "detection wavelength" as used according to the present invention for measuring the change of turbidity in the sample is usually from above about 340 nm to below about 500 nm, preferably from 350, 360 or 370 nm to about 480, 490 or 499 nm, and in particular from about 390 to 470 nm or 400 to 460 nm or 410 to 450 nm, as for example about 415, 420, 425, 430, 435, 440, or 445 nm.

The "accuracy" of an analytical method of the present invention, is the methods ability to accurately determine the concentration of Cystatin C in a sample, compared to the concentration as determined by an even more reliable reference method.

The "precision" of an analytical method of the present invention, is the variation in the results when the concentration of Cystatin C in a sample is determined repeatedly.

A "robustness" of an assay according to the present invention is the methods ability to tolerate interfering substances and variations in assay conditions without influencing the resulting value of Cystatin C concentration determination.

An "inert protein" as used in the context of the invention is a protein of any origin (for example, human or non-human mammalian, microbial) which does not disturb the assay method of the invention; in particular it should have substantially no or no detectable affinity for Cystatin C to be analysed and/or for the antibodies as used in the assay method of the invention.

A Cystatin C "binding" antibody is an antibody which recognizes an antigenic determinant of human Cystatin C and binds thereto specifically or non-specifically. Unless otherwise stated the proportion of anti-human Cystatin C antibodies stated in the present application relates to such "binding" antibodies.

DETAILED DESCRIPTION OF THE INVENTION a) Aspects of the Present Invention

A first aspect of the invention relates to a particle enhanced turbidimetric immunoassay for assessing human Cystatin C in a human body liquid sample or a sample derived there from, by
  (1) forming an assay mixture by contacting said sample or a dilution thereof with a nanoparticle-antibody conjugate (or nanoparticle-immunoconjugate), comprising nanoparticles suitable for turbidimetric measurement, wherein said nanoparticles are coated with anti-human Cystatin C antibodies or antigen binding fragments thereof, to bind said Cystatin C, wherein said coated nanoparticles have a median diameter in the range of at least 40 nm, as for example at least 45, 50, 55 or 58 nm, preferably more than 58 nm, and
  (2) assessing the human Cystatin C content by measuring the change in turbidity of said mixture at one, two or three, preferably one, detection wavelength in a range between above 340 nm and below 500 nm, by determining the change of a suitable optical parameter, like its absorbance.

The "absorbance change" may be expressed in the absolute difference between two (an initial and final) measurement (for example as ABS values) or as a kinetic parameter expressing the absorbance change per time (for example as ABS/min values).

Preferably, the Cystatin C concentration of a sample is determined by measuring the initial rate of the increase of the absorbance, (a) by direct recording at the time of the mixing, or more preferably (b) by recording shortly after the mixing combined with a backwards extrapolation to the initial increase absorbance, or, in particular, (c) by measuring the absorbance difference between two or more time-points less than 1 minute after the mixing of the sample and the reagents.

In a preferred embodiment of the invention the initial rate of absorbance change is determined, and in particular, in at least one, as for example one, two, three or four, but preferably one time interval, of about 5 to 300 seconds starting immediately at or shortly after forming said assay mixture.

"Shortly after" means a few seconds, as for example 1 to 40 or 2 to 30 seconds, in particular 5, 10, 15, 20 or 25 seconds after having mixed all test ingredients together. Preferred time intervals for measurement have a duration of 10 to 280, 50 to 250, 70 to 220, 80 to 210, 100 to 200, 110 to 190, or 125 to 185 seconds, like 130, 140, 150, 160 or 170 seconds and are taken 1 to 40 or 2 to 30 seconds, in particular 5, 10, 15, 20 or 25 seconds after forming said assay mixture. Examples of suitable time intervals are 10 to 290, 15 to 200, 200 to 180 or 25 to 150 seconds after having mixed all test ingredients together.

Preferably said antibodies comprise polyclonal non-human, non-rodent antibodies against human Cystatin C; in particular said polyclonal antibodies comprise avian antibodies against human Cystatin C. Said avian antibodies may be take from avian serum, preferably however, they are derived from egg yolk, i.e. they are an egg yolk fraction.

In a further preferred embodiment at least 25 wt.-% of said polyclonal antibodies or fragments thereof have been obtained by affinity purification with human Cystatin C. By affinity purification the proportion of those antibodies binding to human Cystatin C is increased. In addition it may be possible to further enrich by affinity purification antibodies which bind to human Cystatin C with higher affinity (or avidity) than those antibodies which were removed from the mixture.

For example, a suitable antibody as used according to the invention may have an affinity or avidity for human Cystatin C which corresponds to (or is substantially identical with) the affinity or avidity of an avian (for example polyclonal) antibody obtainable by affinity purification of avian antibody through binding of avian anti-human Cystatin C antiserum to human Cystatin C immobilized on a solid phase and, preferably after washing for example with phosphate-buffered saline, eluting bound antibodies with citrate buffer, of a molarity in the range 0.05 M to 0.2 M, or 0.08 to 0.12 M, in particular about 0.1 M; and a pH in the range of about 3 to 3.5, or 3.1 to 3.3, in particular about 3.2 (as for example explained in more detail in the subsequent experimental part).

In a further embodiment said antibodies comprise (a) monoclonal antibodies binding to a single epitope of human Cystatin C or (b) a set of two or more species of monoclonal antibodies, wherein each species of monoclonal antibodies binds a different epitope of human Cystatin C or two or more species bind identical epitopes with different binding strength (affinity or avidity).

Said monoclonal antibodies are either of human or of non-human (for example originating from a rodent, sheep, goat, bird or rabbit) origin.

The coated nanoparticles as used according to the invention preferably have a mean diameter of more than 58 nm, in particular a mean diameter in the range of 59 to 160, 60 to 140, 70 to 120, 75 to 110, 80 to 105, or 90 to 95 nm. Preferably they are coated with a layer of antibodies. In particular said layer may be considered as monolayer with an approximate thickness of about 5 nm. The layer may be "complete" (particles saturated with antibodies) or, more preferably "incomplete" (i.e. less antibodies are used than the binding capacity of the particle would afford).

In a further preferred embodiment said coated nanoparticles are coated incompletely with about 5 to 35%, in particular 10 to 30% or 15 to 25% binding antibody per total weight of the nanoparticle-antibody conjugate.

In a further preferred embodiment, the nanoparticles are coated with a mixture of antibody and inert, preferably hydrophilic, protein. For example, from 20 to 90%, and more preferred 35 to 80%, and even more preferred 40 to 70% of the total protein bound to the surface of the nanoparticles are constituted by the anti-Cystatin C antibody. Such particles preferably carry antibodies in an amount which is less than the amount of antibodies theoretically attachable to the particles according to the binding capacity of said non-coated particles. At the same time areas of the particle surface not covered by antibody molecules are saturated with inert, preferably hydrophilic protein.

In a preferred embodiment, said original, non-coated nanoparticles are essentially made of latex, polystyrene, polyvinyl chloride, epoxy resin, polyvinylidene chloride, poly-alpha-naphthyl methacrylate, polyvinylnaphthalene, and corresponding copolymers thereof. Other suitable particle materials are available in the art and a skilled reader, guided by the teaching of the invention, will be in a position to make an appropriate selection.

According to a further embodiment of the claimed method the turbidity change is measured via the change in the said assay mixture's absorbance of light at a wavelength in the range of 350 to 499 nm, preferably and at a temperature in the range of 10 to 50 degree Celsius, and preferably be determining the initial change of absorbance "shortly after" starting the reaction in a predetermined "time interval" as defined above.

The present invention also provides turbidimetric immunoassay methods for measuring Cystatin C in a body liquid sample or a sample derived from a body liquid, characterized by forming an assay mixture by contacting said Cystatin C containing liquid sample, or a sample derived from a Cystatin C containing liquid or a dilution of a Cystatin C containing sample, with nanoparticle-bound polyclonal or monoclonal anti-Cystatin C antibodies or antibody fragments, to bind said Cystatin C, and assessing the Cystatin C content by measuring the change in turbidity of the mixture, and the turbidity is further characterized by a change in the said mixture's absorbance of light of a given wavelength, if the mixture is kept for a given period of time at a given temperature after forming said mixture with coated nanoparticles of a certain minimum sizes, as stated above and explained in more detail in the experimental part.

Based on the specific teaching herein, including the enclosed figures and tables, a skilled reader will be able to calculate further values of the change of absorbance observable according to the present invention at different times, temperatures and/or wavelengths.

By way of example, the following values may be obtained:
26 degrees Celcius, time interval 38-208 seconds, median diameter 92 nm; wavelength 405 nm:

| | |
|---|---|
| 0.44 mg Cystatin C/liter | Rate of change: 7.2 mABS Units/min |
| 0.83 mg Cystatin C/liter | Rate of change: 14.1 mABS Units/min |
| 1.38 mg Cystatin C/liter | Rate of change: 25.4 mABS Units/min |
| 2.77 mg Cystatin C/liter | Rate of change: 56.5 mABS Units/min |
| 4.46 mg Cystatin C/liter | Rate of change: 107.3 mABS Units/min |
| 8.05 mg Cystatin C/liter | Rate of change: 199.1 mABS Units/min |

26 degrees Celcius, time interval 38-208 seconds, median diameter 92 nm wavelength 380 nm:

| | |
|---|---|
| 0.44 mg Cystatin C/liter | Rate of change: 9.7 mABS Units/min |
| 0.83 mg Cystatin C/liter | Rate of change: 15.9 mABS Units/min |
| 1.38 mg Cystatin C/liter | Rate of change: 29.14 mABS Units/min |
| 2.77 mg Cystatin C/liter | Rate of change: 62.5 mABS Units/min |
| 4.46 mg Cystatin C/liter | Rate of change: 108.7 mABS Units/min |
| 8.05 mg Cystatin C/liter | Rate of change: 192 mABS Units/min |

A further preferred method according to the invention is characterized by that—when a correlation curve against a nephelometric method is constructed—an intercept value of less than 0.15 mg/l, preferentially less than 0.1 and even more preferred less than 0.05 mg/l of Cystatin is obtained for the turbidimetric method for a corresponding value of 0 mg/l Cystatin C as obtained by the nephelometric method.

A further preferred method according to the invention is characterized by that—when a correlation curve against a non-homogeneous immunoassay method is constructed—an intercept value of less than 0.25 mg/l, preferentially less than 0.15 and even more preferred less than 0.5 mg/l of Cystatin is obtained for a corresponding value of 0 mg/l Cystatin C.

A further preferred method according to the invention is characterized by having an interference from 15 mmol/liter triglycerides in the test sample of less than 6%, preferably less than 4% or even more preferred less than 2% on the measured value of Cystatin C at a level of 1.2 mg Cystatin C per l.

A further preferred method according to the invention is characterized by having a deviation from linearity below 5%, preferably below 4% or more preferred below 3% in a measurement range of 1.32 to 7.5 mg Cystatin C per liter, and/or a deviation from linearity below 15%, preferably below 11% and even more preferred below 7% in the measurement region from measurement range of 0.75 to 1.32 mg Cystatin C per liter.

A further aspect of the invention provides a method for the assessment of the glomerular filtration rate of a mammal, which method comprises the turbidimetric assessment of human Cystatin C according to a method a defined above. Said method may in particular be applied during diagnosis or therapy of renal dysfunctions (like renal insufficiency or failure) or diseases or conditions associated therewith.

Still another aspect of the invention relates to a reagent kit or kit of parts, or set of reagents for the performance of the method as defined above, comprising (a) particles, comprising anti-Cystatin C immunoparticles as defined above in dry or suspended form, (b) an assay buffer in dry or dissolved form, and, optionally (c) calibrator mixture(s) and control mixture(s) each in dry or dissolved or suspended form.

Preferably the particle and the assay buffer are provided in combination either in dry or in suspended form.

According to another aspect of the invention nanoparticle-antibody conjugates according to the above definition and the more detailed description below are provided.

The present invention relates to the use of such nanoparticle-antibody conjugates in an immunoassay for the assessment of human Cystatin C or in a diagnostic method for the assessment of the glomerular filtration rate of a mammal.

Finally, the present invention relates to the use of such nanoparticle-antibody conjugates in an immunoassay for the assessment of human Cystatin C or in a diagnostic method for the assessment of renal dysfunction, as for example renal insufficiency or failure.

b) Preparation of Anti-Human Cystatin C Antibodies b1) Polyclonal Antibodies

Polyclonal anti human Cystatin C antibodies can be prepared by methods well known in the art, such as those described for example by Chase, M. W., 1967,. in "Methods of Immunology and Immunochemistry", ed. Williams, A. et al., M. W., pp. 197-209, Academic Press, New York. Briefly, animals of a suitable species (for example rabbits, goats, or sheep, or, preferably avian species, in particular poultry, like hens) are repetitively immunized with purified antigen in an appropriate adjuvant, for example Freund's complete or incomplete adjuvant. After immunization the animals are bled and the polyclonal antibodies are purified by methods such as for example ammonium sulfate or ammonium chloride precipitation, anionic exchange chromatography, immunoaffinity chromatography, and/or affinity chromatography.

To achieve a sufficient turbidimetric signal, antibodies of high avidity are preferred. Since polyclonal antibodies comprise many different antibody molecules, an affinity constant cannot be calculated, however high avidity and affinity was obtained by conventional polyclonal antibody techniques. Rabbit antibodies obtained by conventional methods were used, however even better results were obtained with sheep antibodies. Even more better results were obtained when avian antibodies were used. The avian antibodies may be according to the methods described in Larsson A, Baaloew R-M, Lindahl T, and Forsberg P-O in Poultry Science 72:1807-1812, 1993. It is contemplated that the avians being genetically more distinct from humans are able to generate antibodies towards human Cystatin C that have a higher avidity than polyclonal mammalian antibodies.

Polyclonal avian antibodies routinely are obtained from egg yolk (and are therefore designated IgYs). Egg yolk, however, contains large amounts of lipids making their further use problematic. IgY can be isolated from egg yolk by using stepwise ammonium sulphate (for example 25 to 40%) and polyethylene glycol (PEG) precipitation. For initial purification also commercial IgY purification kits obtainable from Gallus Immunotch Inc, Cary, USA, or the Eggcellent Chicken IgY Purification Kit, obtainable from Pierce, Rockford, USA may also be employed considering the manufacturer's instructions.

Furthermore, the avidity of polyclonal antibodies may be further increased by using antibodies that ware purified by the use of antigen affinity purification methods, for example according to the teaching in "Affinity Purification of Proteins"(April 2006) and incorporated by reference Affinity purification is described in more detail below.

Increased avidity was in particular observed when 20% of the antibodies used had been antigen affinity purified, even more increase was observed when 50% of the antibodies had been antigen affinity purified and even more when more than 75%, like 75 to 100% of the antibodies had been obtained by antigen affinity purification methods.

For affinity purification of avian polyclonal anti-human Cystatin C antibodies a suitable human Cystatin C affinity column has to be prepared. Purified human Cystatin C is fixed by a standard protocol to a suitable solid supports as for example are Sepharose or Affi-gel, activated to covalently the antigen to the support (suitable activated solid supports are for example available from Pierce, Rockford, USA). An affinity column is then prepared from said antigen-carrying resin.

Successful affinity purification of antibody depends on effective presentation of the relevant epitopes on the antigen to binding sites of the antibody. If the antigen is small and immobilized directly to a solid support surface by multiple chemical bonds, important epitopes may be blocked or sterically hindered, prohibiting effective antibody binding. Therefore, it is best to immobilize antigens using a unique functional group (e.g., sulfhydryl on a single terminal cysteine in a peptide) and to use an activated support whose reactive groups occur on spacer arms that are several atoms long. For larger antigens, especially those with multiple sites of immobilization, the spacer arm length becomes less important since the antigen itself serves as an effective spacer between the support matrix and the epitope.

Little variation normally exists among typical binding and elution conditions for affinity purification of antibodies because at the core of each procedure is the affinity of an antibody for its respective antigen. Since antibodies are designed to recognize and bind antigens tightly under physiologic conditions, most affinity purification procedures use binding conditions that mimic physiologic pH and ionic strength. The most common binding buffers are phosphate buffered saline (PBS) and Tris buffered saline (TBS) at pH 7.2 and 1.5 M NaCl (premixed buffer packs are for example available from Pierce, Rockford, USA). Once the antibody has been bound to an immobilized antigen, additional binding buffer is used to wash unbound material from the support. To minimize non-specific binding, the wash buffer may contain additional salt or detergent to disrupt any weak interactions.

Specific, purified antibodies are eluted from an affinity resin by altering the pH and/or ionic strength of the buffer (common elution buffers are for example available from Pierce, Rockford, USA). Antibodies in general are resilient proteins that tolerate a range of pH from 2.5 to 11.5 with minimal loss of activity, and this is by far the most common elution strategy. In some cases an antibody-antigen interaction is not efficiently disrupted by pH changes or is damaged by the pH, requiring that an alternate strategy be employed.

An example for an affinity purification protocol is given below:

Step 1: Wash the column (~1 ml resin bed) to remove residual protein before each use using 10 column volumes of the following sequence of buffers:

0.2 M glycine, pH 2.8~10 ml 0.1 M $NaHCO_3$, pH 8.5, 0.5 M NaCl~10 ml

Repeat the cycle with the above buffers twice. Then equilibrate the column in TTBS buffer (0.3 M NaCl, 20 mM Tris/Cl, pH 7.8, 0.1% (v/v) Tween-20 and 0.01% $NaN_3$) containing NaCl adjusted to 0.5 M. {

Step 2: Add to 10 ml aliquot of crude antibody preparation, 1 ml 10× TTBS and 0.55 ml 4 M NaCl. Centrifuge the mixture to remove any precipitate.

Step 3: Absorb the antibody batchwise by transferring the affinity resin to the tube (a 15 ml tube) with the serum. Incubate in the cold room. Alternatively, one can apply the serum to the column using a slow flow rate. Manually collected fractions are obtained. Collect the phase that passes through the column and re-apply it a second time using a slow flow rate.

Step 4: Wash the column extensively with TTBS+NaCl to 0.5 M until the $A_{280}$ is less than 0.02. Collect 10 ml fractions of the washes and check the $A_{280}$ of the fractions.

Step 5: Elute the antibody using 0.2 M glycine, pH 2.8, containing 0.02% $NaN_3$. Elute using 1 ml aliquots of buffer. Collect fractions into 1.5 ml microfuge tube containing 50 ml 1 M Tris, pH 8.5. This neutralizes the acidic elution buffer soon after the protein is eluted. Collect at least 10 fractions. This is usually sufficient to remove the antibody. Read the $A_{280}$ of each fraction using an appropriate blank (i.e., 1 ml glycine buffer plus 50 ml 1 M Tris).

Step 6: Pool the appropriate fractions. Get an $A_{280}$ of the pools and store antibodies at 4° C. or consider freezing (−70 ° C.) in aliquots in the presence of 50% glycerol.

Step 7: Wash the column by washing extensively with the 0.2 M glycine, pH 2.8 buffer, followed by TTBS.

b2) Monoclonal Antibodies

Polyclonal antibodies are often more preferred than monoclonal antibodies in particle-enchanced turbidimetric assays. Polyclonal antibodies are inherently reactive to many different epitopes on the antigens (or analytes) (contrary to monoclonals), and therefore more easily create cross-bindings and networks between the antigens molecules per se, and between the antigens and the particles to which the antibodies are immobilized. In contrast, monoclonal antibodies generally bind to one type of epitopes only, which makes it more difficult to form cross-bindings and networks. The diagnostic industry often prefers, however, the use of monoclonal antibodies, because they are easier to standardized and to quality control to a predefined standard, especially over a product life-time of many years. There are, therefore, good examples on the use of monoclonal antibodies for particle enhanced turbidimetric immunoassays, especially when there are antigenic characteristics favoring the use of monoclonal antibodies. Eda & al. in "Development of a New Microparticle-Enhanced Turbidimetric Assay for C-reactive proten With Superior features in Analytical Sensitivity and Dynamic range", J. Clin. Lab. Analysis, 12: 137-144 (1998) describes the use of two different monoclonal antibodies and two different micro particles. CRP is especially favourable for the use of monoclonals, because the CRP molecule is a pentamer of identical subunits—and therefore carries five replicates of all epitopes (Pepys M B & al, Adv. Immunol. 34:141-212 (1983)), which makes the use of monoclonal antibodies much easier. However, also with monomeric and smaller proteins like Cystatin C, cocktails of different monoclonal antibodies may be used in special embodiments of the present inventions.

Cocktails of different monoclonal antibodies, especially when they are composed of many different monoclonal antibodies with high affinity to Cystatin C, will result in good embodiments of the present invention of Cystatin C immunoassays.

Monoclonal anti human Cystatin C antibodies also can be prepared by methods well known in the art, as for example those described by G. Köhler at al., 1975, Nature 256, 495, G. Galfre et al., 1981, Meth. Enzymol. 73, 3-46, or R. Kennet, 1980, in: "Hybridomas: a new dimension in biological analysis", ed. R. Kennet et al., Plenum press, New York & London. Spleen cells or peripheral blood cells from immunized mice or rats are fused with a myeloma cell line, using for instance the polyethylene fusion method. After fusion the cells are grown under suitable conditions, for example on culture plates and a selection of correctly fused cells is performed using for example the hypoxanthine/aminopterin/thymidine (HAT) selection method. Antibody producing cell lines are identified by methods such as EIAs, RIAs or agglutination assays. After identification of the antibody producing cell line, the cells are repeatedly subcloned, as for example by the method of limited dilution, to guarantee that the new growing cell line derives from one single cell.

b3) Chimeric Antibodies

Chimeric anti human Cystatin C antibodies can be obtained by methods well known in the art such as that described by G. L. Boulianne et al., 1984, Nature 312, 643-645. The procedure can be briefly described as follows. The DNA of the antigen-binding site from a monoclonal antibody of one species or parts thereof are transferred to the DNA of the antibody framework of another antibody of a different species. This new construct is cloned into an expression vector, which is transferred to the corresponding expression system to produce the antibody.

b4) Recombinant Antibodies

Recombinant anti human Cystatin C antibodies can be obtained without using animal vehicles by methods known in the art, such as those described by G. Winter et al., 1991, Nature, 349, 293 or J. S. Huston et al., 1988, Proc. Ntl. Acad. Sci. USA, 85, 5879. Those methods involve the following steps: introduction of DNA (cDNA or synthetic DNA) coding for an antibody or fragments thereof into a host cell, for example *E. coli*, fungi, yeast, plants or eucaryotic cells, selection of antibodies with the desired specificity and affinity and expressing the antibody or fragment thereof in the corresponding expression system.

b5) Antibody Fragments

Fab-, Fab'-, and $F(ab')_2$-fragments of polyclonal antibodies, monoclonal antibodies of any species (including chimeric antibodies and or recombinant antibodies) can be prepared by methods well known in the art, such as those described for example by A. Nissonoff et al., 1960, Arch Biochem Biophys, 89, 230, or R. P. Porter, 1959, Biochem J, 73, 119, or E. Harlow et al, 1988, in "Antibodies—A Laboratory Manual", 626-631, Cold Spring Harbour Press, N.Y., USA.

b6) Selection of Anti Human Cystatin C Antibodies of Different Reactivities to the Human Cystatin C When using monoclonal antibodies or fragments thereof as binding partners, the selection of the antibodies of different, in particular high and low reactivity, can conveniently be performed by coating each of the monoclonal antibody separately onto nanoparticles of the same material and size by conventional coating techniques, followed by mixing the nanoparticle reagents in a given ratio, for example 1/1 v/v, in a permutative manner with the analyte. After generating calibration curves of the nanoparticle reagent under the same conditions, the steepness of the resulting calibration curves for low concentrations of analyte gives a first indication of the reactivity of the immunological binding partners.

When using polyclonal antibodies as binding partners, the preparation of high and low reactivity polyclonal antibodies may be performed according to methods well known in the art by introducing the polyclonal antibodies into an affinity chromatography column, carrying the antigenic analyte covalently bound to the gel matrix. With a gradient of elution buffer low reactivity polyclonal antibody fractions will elute first from the column, followed by fractions with increasingly higher reactivity (see S. Yamamoto et al., 1993, "Veterinary Immunology and Immunopathology"36, 257-264, Elsevier Science Publishers B. V., Amsterdam). Reactivity of the fractions can then be checked either with a BIAcore instrument or by coating them independently onto nanoparticles of the same size and material and generating the corresponding calibration curves.

Selection of antibodies can be done by the above mentioned procedure of coating them on nanoparticles followed by a detection limit analysis or a determination of its functional affinity as described above. If appropriate, mixtures of different anti human Cystatin C antibodies differing with respect to their affinity/avidity vis-à-vis human Cystatin C may be used for preparing nanoparticle-antibody conjugates of the present invention. Suitable mixing ratios can be determined by a skilled person by a limited series of experiments.

Suitable anti human Cystatin C antibodies are also commercially available from different sources. For example, HyTest, Finland offers a set of high-affinity anti human Cystatin C antibodies recognizing different epitopes of the antigen. These antibodies are prepared in conventional manner by immunizing Balb/c mice with Cystatin C purified from human urine and producing hybridomas by fusion with the hybridoma cell line Sp2/0. Antibodies produced by selected clones were purified by protein A affinity chromatography. The following mAbs are presently available from HyTest: Cyst10, Cyst13, Cyst16, Cyst18, Cyst19, Cyst23, Cyst24, and Cyst28. Further suppliers for commercially available mono- or polyclonal anti human Cystatin C antibodies are: Fusion, Northern Ireland; BioVendor, Czech Republic, AB Location, Germany; Advanced Immunicemical, USA; Abcam, UK; Axxora, UK; Biodesign, USA; R&D Systems, USA;AbD Serotec, Norway; Strategic Biosolutions, USA. All anti human Cystatin C antibodies of said sources may, in principle, be used alone or in combination for performing the present invention.

c) Nanoparticles and their Conjugates with Antibody

The material for preparing the nanoparticles of the invention may be any natural or synthetic, inorganic, organic, non-polymer or polymer material suitable for generating and performing particle-enhanced light scattering assays. Such materials include for example selenium, carbon, gold; nitrides of carbon, silicium or germanium, for example $Si_3N_4$; oxides of iron, titanium or silicium, for example $TiO_2$ or $SiO_2$; and polymeric materials such as for example, latex, polystyrene, poly(vinyl chloride), epoxy resins, poly(vinylidene chloride), poly(alpha-naphtyl methacrylate), poly(vinylnaphtalene), or copolymers thereof, in particular copolymers of styrene and a copolymerizable ethylenically unsaturated compound, for example styrene-(meth)acrylate co-polymers. Particles made of polymeric materials, as well as core-shell particles consisting of an inner core polymerized from styrene and an outer shell formed by copolymerization from styrene with a copolymerizable, ethylenically unsaturated compound, as described for example in U.S. Pat. No. 4,210,723, are also suitable.

Suitable polymeric particles for conjugation can be purchased from Bangs Particles Inc. or Interfacial Dynamics Inc, Merck SA, France, or other suitable sources. The particles can be activated for binding to antibodies according to numerous methods, a thorough teaching of such coupling chemistry can be found, e.g. in TechNote 205, Rev. 003, for example March, 2002, "Covalent Coupling" (incorporated by reference) which can be downloaded from Bangs Laboratories, Inc.'s web-site. For example, coupling may be achieved by means of particles carrying on their surface carboxyl-, amino-, hydroxyl-, hydrazide- or chloromethyl groups. The molecule to be coupled may either react directly with such groups or by means of a suitable linker, as for example carbodiimides, glutaraldehyde, or cyanogen bromide.

The shell of the particles according to this invention preferably has to comprise antibodies with high affinities for Cystatin C, combined with a nanoparticle core of a certain size to generate a sufficient turbidimetric signal. Typically the nanoparticles comprising the shell of proteinaceous material is between 58 and 200 nm, more preferred between 65 and 150 nm, and even more preferred between 80 and 135 nm.

In a particular embodiment of the invention the mean diameter of non-coated particles is about 80 nm. Using these particles, after coating they are typically 90-100 nanometers in diameter. As a general rule a monolayer of antibodies is about 5nm thick, so that such particles are considered to carry a monolayer of antibodies.

These particles will have good performance when 5 to 35% of the total dry weight of the conjugated particles is constituted by antibodies, better performance at 10 to 30%, and optimum performance when 15 to 25% of the total dry weight of the conjugated particles is constituted by antibodies.

If slightly larger particles are used, these optimal percentage values go down. By way of example, if 95 nm naked particles are used, they typically end up being 110 nm in median diameter if coated. The corresponding percentages are then 4 to 32%, 8 to 26%, and, for optimum performance, 12 to 22% (percentage of the total dry weight of the conjugated particles constituted by antibodies). However, with these slightly larger particles, more particles (in the meaning more weight of particles) has to be used in the assay to have enough binding capacity to create a calibration curve without a flattening of the curve at higher concentration of Cystatin C (the assay calibration curve must have a good dynamic range up to over 8 µg Cystatin C per µl sample), which leads to a much higher absorption background (larger particles and more particles), and a lower signal to noise ratio.

On the other hand, smaller particles will have a higher optimum of antibody percentage in the coated immunoparticle. For example, if non-coated particles of a size of 70 nm are used, the median diameter of the coated particles is typically 80 nm, and a proportion of 18 to 30% antibodies of the total dry weight of the conjugated particles will result in optimum percentages, and less optimal are proportions of 12 to 36%, and even less optimal are proportions of 4 to 42% of antibodies. However, with these slightly smaller particles, less particles (in the meaning less weight of particles) has to be used in the assay to create a calibration curve steep enough at lower concentrations, i.e. below 1 µg Cystatin C per µl sample, and the signal will be lower and also more vulnerable to background noise.

Based on the above explanation a skilled reader will be able to provide, guided by the teaching of the present invention, optimum immunoparticle preparations for different assay conditions.

The coating of the anti human Cystatin C antibodies onto the nanoparticles can be performed adsorptively or covalently according to methods well known in the art which meet the properties of the material used.

According to a preferred embodiment, mixtures of one or more hydrophilic inert proteins with the anti-Cystatin C antibodies should be present during the conjugation/binding of the antibodies to the nanoparticles. The inventors have surprisingly observed that optimal results with hydrophilic particles with a high binding capacity is obtained when antibodies are conjugated to the particles together with hydrophilic proteins having pI values close to the conjugation pH. Best results were obtained when bovine transferrin and albumin were present during the conjugation. However, also other inert proteins may be mixed with the antibodies during conjugation. Non-limiting examples for such hydrophilic, inert proteins are limpet hemocyanin, haptoglobin and other water soluble proteins, without any affinity for the antibodies nor the Cystatin C.

During the coupling process the conditions are or should be, or if necessary should be adapted to be, such that the antibodies are more reactive with the nanoparticle core material than the inert protein so that they will bind more or less quantitatively to the core. Residual reactive portions of the nanoparticle surface will be blocked by the inert protein.

The present inventors observed, as general rule, that in a the first step the hydrophobic parts of the antibodies seem to bind physically to the particles, and thus the whole molecule is close to the reactive, as for example chloromethyl, groups on the particle surface, which then reacts with the corresponding, as for example amine, groups of the protein molecule. Due to this physical absorption, the large antibody molecules surprisingly compete well with the smaller, inert hydrophilic proteins like albumin and transferrin. However—since the used less antibodies than the binding capacity of the particles, the inert proteins, like albumins and transferrins, react with whatever is left to react with on the surface of the particles, and then render particles of the present invention, which have a good hydrophilic surface and a good antibody binding capacity at the same time, and an appropriate proportion of nanoparticle material that can generate a good signal.

Adapting suitable conditions to each coating process variant is, guided by the teaching provided herein, routine for a person skilled in the art.

For example, for coupling a pH half a unit above the pI of the antibody may be chosen when monoclonal antibodies were used. Polyclonal antibodies have a quite diverse pI, and so with polyclonal antibodies pH of 8.8 may preferably be chosen.

In a preferred embodiment, based on the total protein content of the coupling reaction mixture, about 3 to 70 wt.-%, or even more preferred 5 to 40 wt.-% of the protein present during conjugation should be constituted by the anti-Cystatin C antibodies.

Since the antibodies have, as explained above, a higher binding rate to the particles than the hydrophilic inert proteins, the ratio of antibody protein to total protein bound to the surface of the particles will be much higher; for example from 20 to 90%, and more preferred 35 to 80%, and even more preferred 40 to 70% of the total protein bound to the surface of the particles are constituted by the antibodies.

d) Preferred Embodiments of the Claimed Turbidimetric Method d1) Advantages of the Invention The present invention provides a turbidimetric Cystatin C immunoassay with a far stronger signal to noise ratio than in the prior art. By choosing large core and protein shell particles, preferably of a certain minimum size, combined with antigen affinity purified antibodies, a surprisingly high aggregation signal was obtained. A strong turbidimetric signal was obtained due to a surprising synergetic effect between the refractive index of the particles compared to the assay buffer, and the high affinity (or avidity) of the highly purified antibodies. The strong turbidimetric signal led to a higher robustness to interfering substances, e.g. triglycerides, and a better linearity than in the prior art of turbidimetric Cystatin C immunoassays.

The critical factor for a homogeneous immunoassay is the signal generated per mass unit per volume of assay mixture. The assay mixture is the mixture obtained when all reagents and the sample have been added. For example, if a sample of 3 µl is to be analyzed, and the said sample contains 1 mg/l Cystatin C, and the final volume after mixing all reagents and sample is 300 µl, the concentration of Cystatin C in the final assay mixture is 10 µg/l. If the concentration of the analyte in the sample is low, this can often be compensated by using a larger sample compared to the assay mixture volume, e.g. increasing the sample to 6 µl in an assay mixture volume of 300 µl. There are several obstacles to increasing the sample volume. Firstly, the concentration of all interfering substances that might be in the sample is increased in the assay mixture. Secondly, the need for antibodies to overcome the critical hook effect (i.e. dose/response curve with negative slope) is increased, which in turn, increases the antibody costs of the assay correspondingly.

There is therefore a requirement to obtain good signal strength and robust assays at a low assay mixture concentration of the analyte, and a corresponding low sample volume. Increasing the sample volume in homogeneous immunoassays leads to more interference and to more expensive assays.

The present invention provides a surprising increase in signal strength, robustness and linearity of turbidimetric Cystatin C immunoassays. The present invention also has less interference from lipids such as triglycerides. It was accomplished after understanding the shortcomings of the prior art being based on a too-low signal strength in the turbidimetric signal per mass unit of analyte, and provides a methods with better precision, linearity and less interference than the turbidimetric methods in the prior art.

d2) Performing the Assay Method of the Present Invention

In a preferred embodiment of the present invention an assay buffer is mixed with a sample and an immunoparticle suspension, and the turbidity of the mixture or the resulting suspension is monitored by a photometer, preferentially a recording photometer, and further preferentially a recording spectrophotometer. A preferred sequence of steps is: mixing the sample in the assay buffer, allowing the mixture to fully dissolve and stabilize, and then adding the immunoparticle mixture. The present invention can also be performed by mixing the assay buffer and the immunoparticle suspension first, and then adding and mixing the sample. Optimal mixing methods (selected among methods well known in the art) should be applied, which can be determined by means of a limited number of pre-experiments.

When a recording photometer is used, the initial rate of the increase of the turbidity can be determined, either by determining the Cystatin C concentration of a sample by measuring the initial rate of the increase of the absorbance, either by direct recording at the time of the mixing, or by recording shortly after the mixing combined with a backwards extrapolation to the initial increase absorbance, or by measuring the absorbance difference between two or more time-points less than 1 minute after the mixing of the sample and the reagents (see above).

These measurements or combined measurements can be correlated or compared to corresponding results with calibrators of known Cystatin C concentration, and the concentration of unknown samples can thus be calculated. These ways to record absorbance values and to compute results are very well known for numerous other substances to be measured by the skilled man of the art of clinical chemistry. Of course, the very good signal derived from the present invention makes such measurements and calculations much more robust and accurate, especially when good signals shortly after the mixing of the sample and the reagents are obtained as described above.

There are several assay buffer mixtures that can be used, with different kinds of buffer substances, with different kinds of detergents and/or different kinds of polymers and/or salts added to the buffer.

TRIS buffer, phosphate buffer, borate buffer and other buffer substances, like MOPS, PIPES, HEPES can be used, and are not critical to the present invention, as long as the assay can maintain a well regulated pH of the final assay mixture, independent of the pH and the buffering capacity of the sample added. Typically the buffer is added in a final molar proportion of about 5 mM to 0,2 M or 10 mM to 0.1 M. The pH is adjusted in the range of 6 to 8, in particular 6.5 to 7.5.

Furthermore, several detergents can be used, as long as they are able to dissolve any lipid content of the sample added, and do not interfere too strongly with the antibodies' reaction with Cystatin C introduced with the sample. Triglycerides, cholesterols and a range of lipoproteins are examples of interfering substances in turbidimetric assays, because the lipids form micro droplets and micelles that give interfering signals. TWEEN® 20 (Polyoxyethylene (20) sorbitan monolaurate; hereinafter "TWEEN® 20"), TRITON® X-100 (octyl phenol ethoxylate; "TRITON® X-100") and deoxycholates are examples of suitable detergents. Measuring Cystatin C in lipid-containing samples is a big challenge, and needs good solubility of the lipids, but even more importantly, a strong signal that overrides any minor interference. Detergents are typically added in a final proportion of 0.01 to 0.5%, or 0.1 to 0.3%, each by weight of the final reaction mixture.

The most widely used polymers are polyethylene glycols of different molecular sizes (in particular of about 6.000 to 8.000), but dextrans and other polymers are can also be used. The polymers have the disadvantage that—when the concentration is too high—they create unspecific precipitation of the other substances introduced when the test sample is mixed into the assay mixture. On the other hand, the said polymers at the same time increase the signal. However, they tend to reduce the overall binding capacity of the immunoparticles. Polymers are typically added in a final proportion of about 0.05 to 0.5% or 0.1 to 0.3%, each by weight of the final reaction mixture.

Suitable salts to adapt the ionic strength are for example alkali metal halides, in particular sodium chloride, added in a concentration of 1 to 100 mM, or 5 to 50 mM.

Further suitable constituents which may be present in the assay mixture are:

amino acids, like glycine, added in final concentrations of about 1 to 50 mM or 5 to 20 mM;

proteins, like albumin added in final proportions of 0.1 to 5 g/l or 0.5 to 2 g/l;

antimicrobial agents, like sodium azide, added in final proportions of 0.1 to 10 or 1 to 5 g/l;

calibrators or control substances: These are typically solutions comprising known concentrations of Cystatin C dissolved in a buffer substance, typically a phosphate buffer or TRIS buffer, optionally with some proteinaceous material, optionally comprising human or animal serum up to 100 volume % (if 100 volume % is serum, then there is no room and no need for the buffer solution.)

Furthermore, one or more of the reagents can be used in a dry, optionally lyophilized form. The antibodies conjugated to the nanoparticles can be used in a dry form, e.g. as a pellet, and be dissolved before use, or can be dissolved into the assay buffer reagent or into to reaction mixture. One or more of the components in the reaction buffer can be added in a dry form before or during the performance of the assay, so also the calibrators. Even the samples can be provided in a dried or lyophilized form, and added to the reaction mixture in a dry form, or being dissolved prior to its use.

In clinical chemistry analysis, the use of standard curves for calibration purposes is standard practice. Thus, in the performance of the method of this invention, samples of known Cystatin C content may be used in the place of clinical samples to construct a standard curve for the response/signal to be measured and the Cystatin C content of the unknown samples may then be calculated by interpolation from the standard curve.

The total concentration of nanoparticle-immunoconjugates in the mixture will be selected according to methods well known in the art of particle enhanced light scattering immunoassays, so that absorbance values deriving from said nanoparticles do not influence accurate and precise measurements but the microparticle concentration is high enough to get signal development. The amount is, of course influenced by different parameters, like the volume of the body fluid sample or the sample derived there from, as well as Cystatin C content.

As non-limiting typical parameters of an assay the following may be mentioned:

A typical sample volume is 1 to 20 µl, as for example 2 to 10 µl, or in particular 3 µl.

A typical immunoparticle volume is 10 to 100 µl or 20 to 60 µl, or in particular 40 µl. Said immunoparticles may be provided as a suspension of 0,5 to 10 or 1 to 5, typically about 2 to 3, in particular 2,26 mg particles per ml buffer solution. The buffer may have a pH in the range of 6 to 9, as for example 7 to 8,5, typically about pH 8.4 Said buffer solution may contain in addition to the buffer substance further ingredients as for example amino acids, salts, inert proteins and emulsifiers or solubilizers as defined above. A typical mixture of such ingredients and buffer comprises 10 mM borate buffer, 10 mM glycine, 15 mM naCl, with 0.25% TWEEN® 20 and 1 g/l albumin.

A typical total assay volume is 100 to 1000 µl, or 200 to 500 µl, or 250 to 300 µl or in particular about 280 µl.

Different instruments run with different total volumes, so that 30% or 60% of these volumes or 150% or 300% of these volumes are typical for other instruments. The ratio between sample volume and the immunoparticle volume can be anything between 1/100 to 2/3, more preferred 2/100 to 1/3, and even more preferred 1/40 to 1/5.

d3) Medical Uses

The assay method of the present invention may be used for the diagnosis and monitoring of pathological or potentially pathological conditions which are related to or manifested in the Cystatin C content of body fluids or tissues. These include in particular the glomerular filtration rate (GFR, as a measure for the kidney function) of a mammal or pathological conditions affecting said filtration rate.

The claimed method may be used to determine the GFR in children; or the GFR of patients with muscle atrophy; to supervise the effects of cancer therapy in kidney function; to supervise renal transplantation and immunosuppressive therapy; to supervise renal filtration rate in diabetes; for detection and management of eclampsia; and to find the correct dosage of drugs in case drug administration is associated with a decrease of GFR which may result in an undesired drug accumulation in the body.

The assay method may also be used for the evaluation of the effects of pharmaceutical on said filtration rate.

A skilled reader of the present description may become aware of further potential applications.

The present invention also provides a set of reagents for the performance of the immunoassay according to this invention.

The reagent set is characterized by comprising anti-Cystatin C immunoparticles, a suitable assay buffer and, optionally calibrator solution(s) and control solution(s). Optionally, the particle suspension and the assay buffer are delivered as a combined reagent.

In another aspect the invention provides an analytical product, optionally in kit or kit-of-parts format, for use in the assay of Cystatin C in a sample, said product comprising: at least on type of nanoparticle-immunoconjugates as described above in dried or suspended form, and optionally one or more further constituents as defined herein, as for example, a suitable assay buffer and, optionally calibrator solution(s) and control solution(s).

The present invention also provides a set of reagents for the performance of the immunoassay according to this invention. The reagent set is characterized by comprising anti-Cystatin C immunoparticles, a suitable assay buffer and, optionally calibrator solution(s) and control solution(s). Optionally, the particle suspension and the assay buffer are delivered as a combined reagent.

Optionally, means for signal assessment may also be present, like a calculator schemes allowing to directly correlate the observed Cystatin C concentration with the GFR parameter.

The following non-limiting examples illustrate in a non-limiting manner the method of the invention.

Experimental Part

SYNTHESIS EXAMPLE 1

Preparation of Polyclonal Avian Serum and Affinity Purification Thereof a) Preparation of Avian Antibody Fraction.

The following immunization protocol may be used for the generation of polyclonal IgY antibodies against human Cystatin C:

Two to four hens are used for each immunization experiment. A couple of eggs are collected before immunization begins. IgY purified from these eggs will serve as the control IgY. 100 µg of highly purified human Cystatin C (purified from urine of patients with tubular proteinuria, commercially available from Scipac Ltd., UK) in phosphate buffer was emulsified with Freund's complete adjuvant and injected into the breast muscle of hens. The injection was repeated every 4 weeks. 10 weeks after the start of the injections, eggs were collected. The egg yolk was isolated from the eggs, and the IgY fraction from the egg yolk was isolated by ammonium-chloride precipitation, in a conventional manner according to prior art methods of egg antibody isolation (see for example Larsson A, Baaloew R-M, Lindahl T, and Forsberg P-O in Poultry Science 72:1807-1812, 1993).

b) Affinity Purification of Polyclonal Antibody Fraction.

10 mg of highly purified human Cystatin C was immobilized on a HITRAP NHS-Active HP column from Amersham Pharmacia Biotech, following the prescription in the package insert of the column.

The isolated IgY fraction was diluted to 2 mg/ml in phosphate buffered saline. 200 ml of this IgY solution was passed through the column, followed by 50 ml phosphate buffered saline with no IgY. The antibodies with specific affinity for the immobilized Cystatin C was eluted with 35 ml of 0.1 molar citrate buffer pH=3.2. The eluted specific anti-Cystatin C antibodies were dialyzed against phosphate buffered saline and concentrated to 3 mg/ml using an Amicon Centircon centrifugation filtration device with molecular weight cut-off of 30.000 Dalton.

SYNTHESIS EXAMPLE 2

Preparation of Monoclonal Anti-Human Cystatin C Antibodies

The preparation of monoclonal anti-human Cystatin C antibodies may be performed as follows by making use of methods well known in the art, described for example by Harlow et al., 1988, Section 6 of "Antibodies: a Laboratory Manual", Cold Spring Harbor Press, N.Y., USA. Human PSA was isolated from human seminal plasma as described Sensabaugh et al., 1990, J. Urology 144, 1523.

Mice were immunized in regular intervals with 4 injections of 50 pg human Cystatin C in RAS (RIBI adjuvant system). Four months after the first injection lymphocytes isolated from the spleen of the immunized mice were fused with the myeloma cell line SP2/0-Ag14 using the polyethyleneglycol method as described by G. Galfre et al., 1981, Methods in Enzymology, 73, 3-46.

Hybridomas secreting an antibody against Cystatin C were identified by the following screening ELISA: microtiterplates were coated with rabbit anti-human-Cystatin C immunoglobulin; Cystatin C bound to this solid phase, was incubated with the supernatants of the hybridoma cultures. Monoclonal antibody bound to Cystatin C was detected using anti-mouse-immunoglobulin-peroxidase-conjugate.

Several hundred hybridomas may be isolated, secreting antibodies against different epitopes of human Cystatin C. The corresponding monoclonal antibodies are then affinity purified and can be characterized in more detail.

Epitope binding was performed and the relative reactivity of the antibodies was determined in terms of their apparent dissociation constants, using the BIAcore biosensor technology (Pharmacia, Sweden). The latter is based on the surface plasmon resonance technique (see J. L. Daiss et al., 1994. in "Methods: A Companion to Methods in Enzymology" 6, 143-156, Academic Press Inc., NY, USA) and allows to monitor the kinetics and stochiometry of biomolecular reactions.

Starting from cell culture supernatants, the monoclonal antibodies were bound to the biosensor surface via polyclonal rabbit anti-mouse-Fc-antibody. Association and dissociation of the antigen Cystatin C to the monoclonal antibodies were monitored. The data may be analysed using the inherent BIA evaluation software, based on the simple A+B=AB equilibrium model (L. G. Fagerstam et al., 1992, Journal of Chromatography, 597, 397-410). The obtained antibodies may then be compared with respect to their respective apparent dissociation constants. Suitable antibodies or combinations thereof may then be used for preparing the immunoparticles of the invention.

SYNTHESIS EXAMPLE 3

Preparation of Anti-Cystatin C Immunoparticles a) Coupling Process—Standard Procedure:
(1) Buffers & Reagents

| MES Buffer | 0.01M | pH 6 |
| Borate Buffer | 0.05M | pH 9.3 |
| PBS Buffer | 0.05M | pH 7.2 |

| | | |
|---|---|---|
| Storage Buffer | 0.05M TRIS | pH 8.4; 1 g/l glycine; 1 g/l TWEEN ® 20 2 g/l albumin, 1 g/l transferrin |
| Antibody | | Ab of your choice at a concentration of 1.0 mg/ml in MES |
| UltraClean Chloromethyl Latex | | As supplied at 4% solids. |

In order to have more signal from the polymer particles per mg of antibody the pH of coupling buffer was adapted in a specific way to the pI of the antibodies to be coupled. In addition the antibodies were diluted with albumin/transferrin prior to coupling (see below). For coupling a pH half a unit above the pI of the antibody was chosen when monoclonal antibodies were used. Polyclonal antibodies have a quite diverse pI, and so with polyclonal antibodies pH of 8.8 was used. The chosen pH was obtained by mixing the above mentioned PBS and borate buffers.

The following standard procedure outlines both a simple one step method for the attachment by physical adsorption of antibodies to chloromethyl. The protocol is for a 1 μm chloromethyl latex at 1% solids. This reaction can easily be scaled up or down to fit individual needs. For example if a different particle size is used then the amounts of antibody (Ab) can be calculated from:

Weight of Ab=(Weight of Ab for 1 μm-particle)/(particle diameter in μm)

(2) Preparation of Latex Particle Suspension
1. Pipette 2.5 ml (40 mg/ml) Chloromethyl latex microspheres and dilute with 10 mL MES buffer.
2. Centrifuge the mixture to sediment the particles; ~3,000 G for ~20 min.
3. Remove supernatant and re-disperse the pellet in 10 ml MES buffer.
4. Centrifuge again and remove the supernatant from the particles.
5. Re-suspend pellet in 5 ml MES buffer, being sure to completely suspend microsphere particles.

The latex suspension is now at approx. 2% solids (i.e. ~20 mg/ml).

(3) Coupling
1. To a 5 ml solution of 1.5 mg antibody, 3.75 mg albumin and 7 mg of bovine transferrin in PBS/borate buffer adjusted to the appropriate pH (see above) 5 ml of the latex is added. This is less than a monolayer of antibody would require. The antibodies are more reactive with the latex than the transferring and the albumin, and bind more or less quantitatively with the latex, and the rest of the latex surface is saturated albumin and/or transferrin. This mixture also ensures against aggregation and good hydrophilicity of the particles. Also other inert proteins may be mixed with the antibodies during conjugation, like limpet hemocyanin, haptoglobin and other water soluble proteins, without any affinity for the antibodies nor the Cystatin C.
2. Incubate latex/protein mixture with gentle mixing at room temperature overnight.
3. Centrifuge to separate the protein-labelled latex particles from unbound protein.
4. Remove and retain supernatant for protein determination.
   At this step, the supernatant can be reserved and a protein determination made. Any residual protein in the supernatant can be subtracted from the original amount added. The remainder is coated on the particles. The only method for protein determination compatible with latex microspheres is the Micro BCA Protein Determination Kit from Pierce.
5. Resuspend the pellet in 10 ml PBS.
6. Centrifuge again to sediment the particles.
7. Repeat steps 5-6 twice more for a total of 3 washes.
8. Re-suspend the final latex in 10 ml Storage Buffer giving a final concentration of 1% solids. Store at 4° C. until used. Do not freeze.

Glycine is used in the storage buffer to fill any reactive sites on the microsphere surface which have not been covered by the protein. This is to reduce non-specific binding. Inert proteins as bovine Serum Albumin (BSA) or bovine transferring may be used for the same purpose if desired. The $NaN_3$ is present as a biocide. If the latex is kept sterile, $NaN_3$, which is not compatible with cell or tissue culture, can be omitted.

b) Preparation of Coated Nanoparticles

The above standard procedure was applied to coat latex particles with a diameter of 0,08 μm for preparing nanoparticle-conjugates of the present invention. According to the above formula 24 mg of antibody and 65 mg of albumin were used to coat 100 mg of particles.

Said anti-Cystatin C immunoparticles were produced by coupling anti-Cystatin C anti-bodies from Norwegian Antibodies AS, produced according to specification given by Gentian AS as given above in Synthesis examples 1 and 2, Norway (said polyclonal anti human Cystatin C antibodies correspond to the affinity purified immunoglobulin fraction of immunoglobulins isolated from the eggs of hens immunised with Cystatin C from patients with chronic renal tubular proteinuria; the affinity purification process was performed with immobilised human Cystatin C), to chloromethyl activated latex particles (0.083 μm, from Intefacial Dynamics Inc., USA, product number C37487). For said coupling the protocol "Coupling of Proteins to IDC Ultraclean Chloromethyl Latex"may be used.

Alternative particles and coupling protocols can be found at Interfacial Dynamics website, Invitrogen's website and Bangs Particles Inc.'s website.

The obtained particles are used as a suspension of 2.26 mg particles per ml in 10 mM borate buffer, 10 mM glycine, 15 mM NaCl, with 0.25% TWEEN® 20 and 1 g/l albumin.

ASSAY EXAMPLE 1

Turbidity as Determined at Different Wavelengths in Cystatin C Assays of the Present Invention a) Reagents The immunoparticle suspension as prepared by Synthesis Example 3 was used in the following experiments:

In said experiments the following optimized assay buffer pH=7.2 was used:
polyethylene glycol (Sigma) 22 g/l,
TWEEN® 20 (Sigma) 3 g/l,
MOPS (Sigma) 9.4 g/l,
sodium azide 2.7 g/l,
sodium chloride 27 g/l, A sample with a Cystatin C concentration of 8 mg/l was used for determining time dependent turbidity change at wavelengths in the rage between 400 and 700 nm.

b) Instrument: Hitachi 917 instrument with standard accessories as provided by Roche Diagnostics, using the spline mode setting, at 37 degrees Celsius.

c) Procedure

Figure 2:
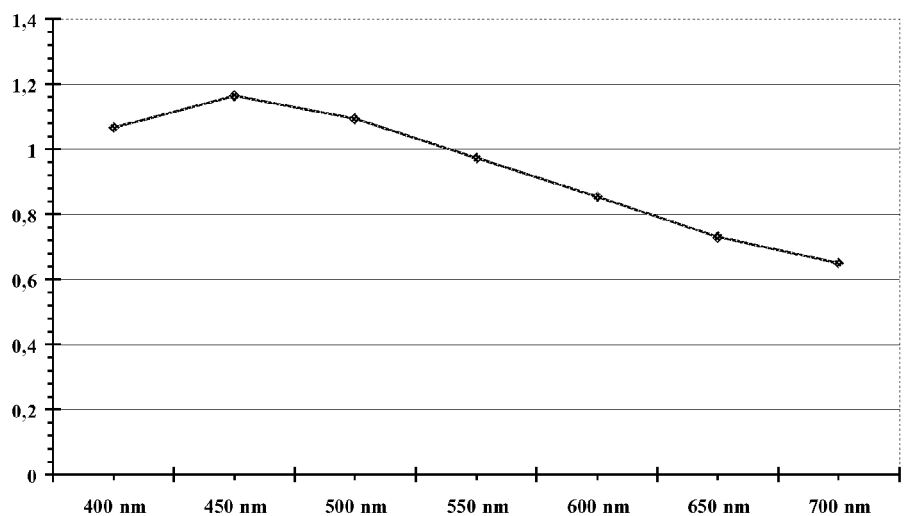
FIG. 2 shows the change of turbidity/absorbance as observed for different wavelengths measured 5 minutes after starting the reaction, using an Hitatchi 917 instrument from Roche Diagnostics.

3 μl sample was mixed with 160 μl of the assay buffer, and allowed to stand for 3 minutes, followed by adding 45 μl of immunoparticle suspension and mixing. After said mixing, the turbidity was measured at different wave lengths and different time points.

d) Results:

The observed results are summarized in FIGS. 1 and 2.

As can be taken from FIG. 1 the background at the start point of the reaction is dependant on the wavelength at which the absorbance is measured, with increasing background with decreasing wavelength.

However, it has now, surprisingly, been observed that from about 340 nm to below about 500 nm, a high net change in absorbance is obtained, with an acceptably low absorbance in the start of the reaction (see FIG. 1).

In addition, a determination of the change in turbidimetry/absorbance showed at different wavelengths and a fixed incubation interval (5 minutes before measurement), that a maximum turbidity is obtained at about 450 nm, (see FIG. 2).

ASSAY EXAMPLE 2

Determination of an Optimum Range of Absorbance Change a) Reagents

Immunoparticles and assay buffer as defined in Assay Example 1

Serum sample with a Cystatin C concentration of 8.3 mg/l b) Instrument: Schimadzu UV-160 spectrophotometer; quarts cuvette with a 10 mm light pathway c) Procedure Experiment (1): 680 µl assay buffer was mixed with a 10 µl serum sample comprising in a quarts cuvette with a 10 mm light pathway, instrument setting in spectrum mode. Thereafter, 180 ul anti-Cystatin C immunoparticles was mixed, and the absorbance spectrum from 350 to 600 nm was measured with a Schimadzu UV-160 spectrophotometer at 0, 1, 2, 3, 4 and 5 minutes after the final mixing. (see FIG. 3a).

Experiment (2): In a separate parallel experiment, the absorbance at 430 nm was measured continuously for five minutes with the instrument setting in kinetic mode. (FIG. 3b).

Figure 3A:
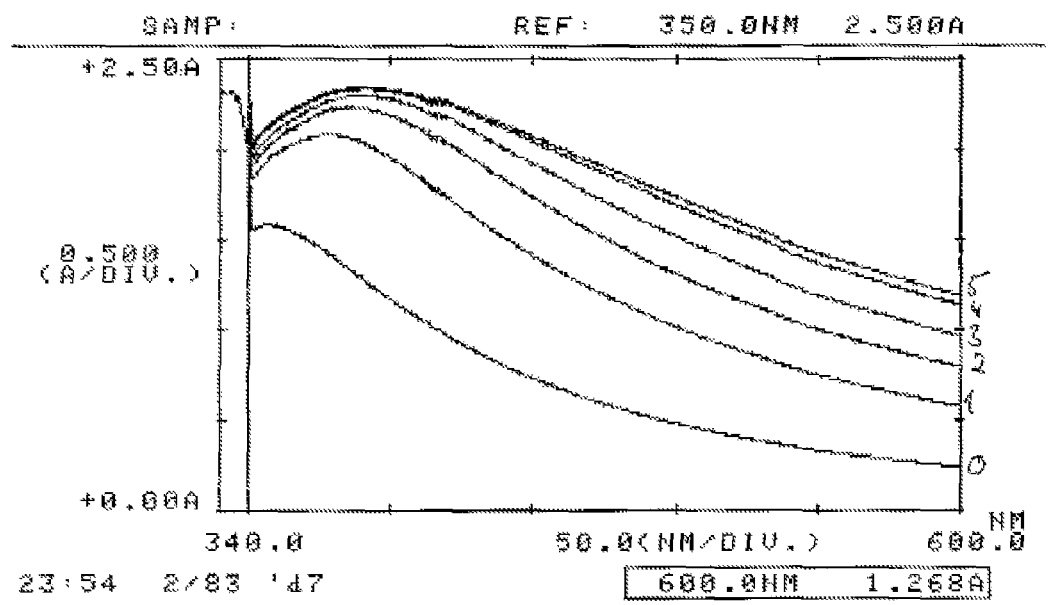
FIG. 3a shows the absorbance spectra in a wavelength range of 340 to 600 nm for an assay sample taken 0, 1, 2, 3, 4 and 5 minutes after the final mixing step (i.e. start of the reaction). The upper graph shows an indicator line at 340 nm and the lower graph an indicator line at 430 nm.

All experiment was performed at room temperature.

d) Results:

The observed results are summarized in FIGS. 3a (Experiment (1)) and 3b (Experiment (2)).

FIG. 3a demonstrates that the best signal increase was obtained around 430 nm (indicated with an indicator line at 430 nm), but with a good signal increase also down to 360 nm and up to 500 nm. Above 500 nm, the signal increase is weaker. From 400 nm and downwards to 350 nm the signal increase is lower, and below 400 nm the zero signal is also very high, resulting in a low signal-to-background ratio.

FIG. 3b demonstrates at 430 nm an initial (measured from 20 to 40 seconds after mixing, as it needs a few seconds before the mixture is homogeneous, therefore a measurement from time 0 is not possible) absorbance change of 251 mAbs Units, corresponding to 753 mAbs Units per minutes. The agglutination reaction continued for 5 minutes and after 5 minutes only a small increase was observed.

It is well understood that the observed rate can be increased or decreased by changing the amount of immunoparticles, the sample volume, the temperature, the composition of the assay buffer, the size of the particles etc. However, the example illustrates that the signal of the reaction increases below about 500 nm down to about 400 nm, below about 400 nm it starts to decrease, and below about 360 nm the signal is even lower. The signal-to-background ration becomes low below about 400 nm, and very low below 360 nm.

Therefore, it can be concluded that there is an intermediate range of wavelengths from about 370 to about 500 nm, with an optimum at around 410 to 450 nm, where the absorbance change is optimal.

Furthermore, it can be taken from FIGS. 1, 3a and 3b that—within a wavelength range of between about 370 and 500 nm—the change of absorbance is highest at the start of the reaction, especially within the first 2 to 3 minutes, and then decreases after three minutes.

Said Figures also demonstrate that time can be saved by measuring earlier after mixing the reagents, which is important for the through-put in the automated analyzer systems. Furthermore, the measurements should not start too early after mixing, because it takes a few seconds before a good mixing has resulted in a homogeneous mixture.

Furthermore, a kinetic reading at many time points during a shorter time period can result in a higher precision than simply measuring two—or a few—time points spread apart. In a multi-analyzer it might not be possible to follow one sample continuously—often the instruments operate carrousels, where the samples are measured many times at a few seconds interval—but repeated measurements in the early stage of the reaction can give better results and higher yield of results (e.g. more results per hour) than waiting until the reaction has flattened out (and end-point measurement).

Therefore, measuring the absorbance at times points between 5 and 280 seconds after mixing all the reagents is preferred, and even more preferred are measurements between 15 and 200 seconds, as for example between 25 and 150 seconds.

ASSAY EXAMPLE 3

Determining the Change of Absorbance at Different Wavelengths and Different Cystatin C Concentrations using a Johnson & Johnson's Vitros 5.1 Instrument The instrument was set to a two point rate mode, with a cubic spline calibration curve setting.

a) Reagents: see Assay Example 1 b) Procedure:

187 µl reagent buffer, 2.4 µl sample at different Cystatin C concentrations (see below), and 60 µl immunoparticles were mixed, followed by measurements at 405—in one experiment—and 380 nM—in another experiment—in a time interval between 38 seconds and 208 seconds after mixing all the reagents. Experiments were performed at 37 degrees Celsius.

c) Results:

Experimental results at 405 nm:

| | |
|---|---|
| 0.44 mg Cystatin C/liter | Rate of change: 7.2 mABS Units/min |
| 0.83 mg Cystatin C/liter | Rate of change: 14.1 mABS Units/min |
| 1.38 mg Cystatin C/liter | Rate of change: 25.4 mABS Units/min |
| 2.77 mg Cystatin C/liter | Rate of change: 56.5 mABS Units/min |
| 4.46 mg Cystatin C/liter | Rate of change: 107.3 mABS Units/min |
| 8.05 mg Cystatin C/liter | Rate of change: 199.1 mABS Units/min |

Experimental results 380 nm:

| | |
|---|---|
| 0.44 mg Cystatin C/liter | Rate of change: 9.7 mABS Units/min |
| 0.83 mg Cystatin C/liter | Rate of change: 15.9 mABS Units/min |
| 1.38 mg Cystatin C/liter | Rate of change: 29.14 mABS Units/min |

-continued

| | |
|---|---|
| 2.77 mg Cystatin C/liter | Rate of change: 62.5 mABS Units/min |
| 4.46 mg Cystatin C/liter | Rate of change: 108.7 mABS Units/min |
| 8.05 mg Cystatin C/liter | Rate of change: 192. mABS Units/min |

Figure 3A:
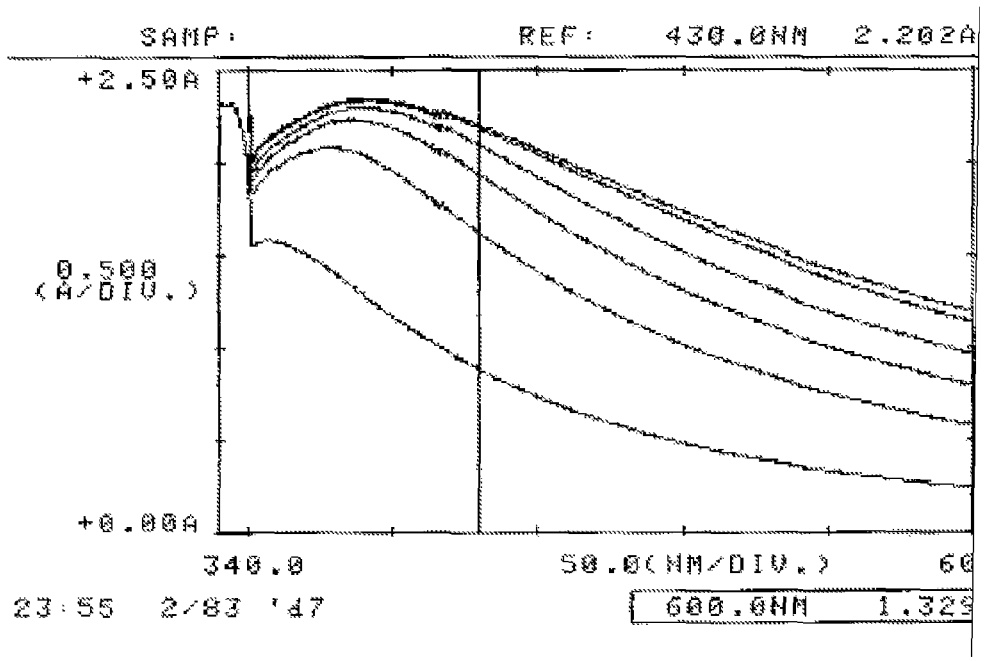
Figure 3B:
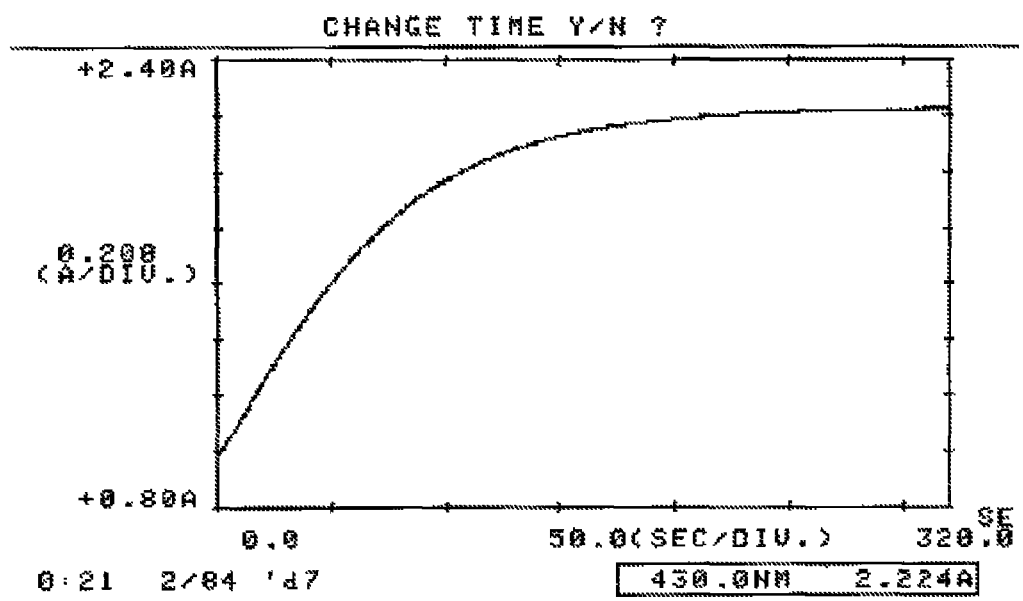
FIG. 3b shows an example of an absorbance change observed at 430 nm measured for a period 320 nm after mixing.

As can be seen, the maximum rate of absorbance change for a sample comprising 8.05 mg Cystatin C/l at 380 nm is lower than at 405 nm. This could be expected, since the maximum absorbance/turbidity decreases if the wavelength is decreased to a value below 450 nm) (as can be seen in FIG. 2 above) while the background signal (the absorbance signal at the start of reaction) goes drastically up when the wavelength is decreased to a value below 450 nm, as can be seen in FIGS. 1 and 3 above. Measuring wavelength values lower than 370, and especially wavelengths as low as 340 (as taught by Newman et al.), therefore, are not recommendable.

ASSAY EXAMPLE 4

Figure 4:
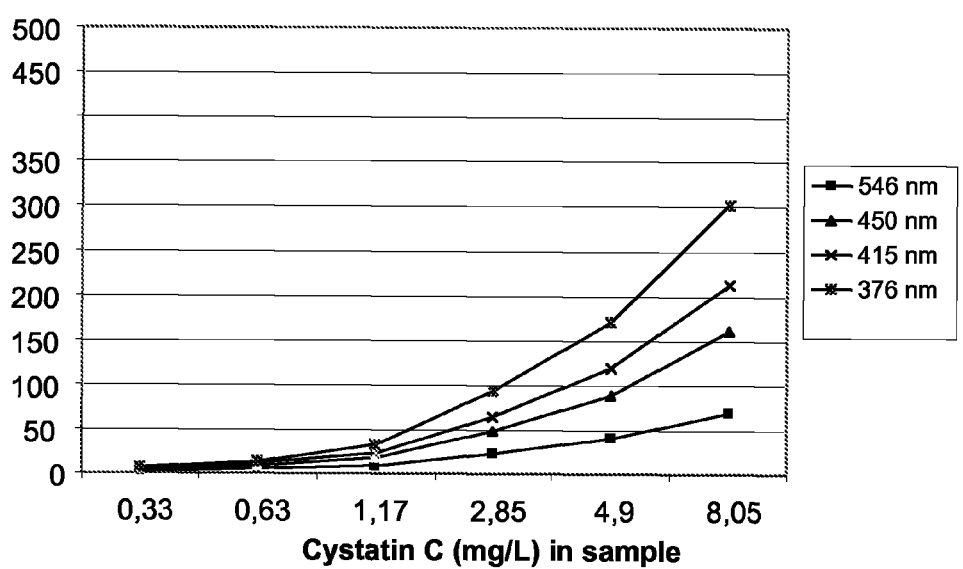
FIG. 4 shows the absorbance change (in milliabsorbance units (mABS)) per minute for different wavelength values as measured in the period of 15 to 70 seconds after mixing all samples, in an Hitatchi 917 instrument.

Determining the Change of Absorbance at Different Wavelengths and Different Cystatin C Concentrations using a Hitatchi 917 Instrument from Roche Diagnostics The instrument is running at 37 degrees Celsius, and a spline calibration curve and a two pint rate were applied.
a) Reagents: see Assay Example 1
b) Procedure:
A 3 µl sample (Cystatin C concentrations see in FIG. 4) was mixed with 230 µl assay buffer and 40 µl water, incubated for 3 minutes, and then mixed with 40 µl immunoparticles. The absorbance changes were measured from 25 to 80 seconds after all reagents having been mixed.
c) Results:
The results are shown in FIG. 4. In this rate experiment, where all measurements have been finalized within 70 seconds after mixing the reagents, the signal is best at the low measuring wavelength of 376 nm, approximately 35% higher than at 415 nm, since only the very first part of the reaction is measured. mAbs/min values are shown in FIG. 4.

ASSAY EXAMPLE 5

Determining the Change of Absorbance at Different Wavelengths and Different Cystatin C Concentrations using a Cobas 501 Multianalyser a) Reagents: see Assay Example 1
b) Procedure/Instrument Setting:
The instrument was set to—In each assay—to mix 170 µl assay with 2.4 µl of sample, followed by mixing of 45 µl immunoparticles to the assay mixture. The Cobas 501 instrument operates in cycles of 8.6 seconds. The instrument was set to having mixed all reagents after 34-35 cycles. The absorbance change at 450 nm was measured from Cycle 36 to cycle 41, in a two point rate setting.
The following rate of change of absorbance was obtained:

| Cystatin C in sample (mg/l) | Rate of absorbance change mABS/min |
|---|---|
| 0.33 | 11 |
| 0.63 | 20.8 |
| 1.17 | 41.2 |
| 2.85 | 113.3 |

-continued

| Cystatin C in sample (mg/l) | Rate of absorbance change mABS/min |
|---|---|
| 4.90 | 228.1 |
| 8.05 | 445.7 |

Using this standard curve and the instrument's spline function for constructing the standard curve, assay results for Cystatin C in unknown serum samples were compared to results obtained with the Prospec nephelometric reference method. Excellent correlation with the reference method was obtained.

| Prospec mABS/min | C501 mABS/min |
|---|---|
| 0.765 | 0.77 |
| 1.045 | 1.0365 |
| 1.22 | 1.188 |
| 1.57 | 1.535 |
| 2.04 | 1.99 |
| 2.355 | 2.2795 |
| 3.19 | 3.12 |
| 4.97 | 4.7095 |
| 6.255 | 5.676 |
| 7.225 | 6.4595 |
| 1.275 | 1.2485 |
| 2.32 | 2.246 |
| 1.12 | 1.129 |
| 1.13 | 1.1165 |
| 1.345 | 1.323 |
| 1.11 | 1.103 |
| 1.395 | 1.3595 |
| 2.575 | 2.503 |
| 1.445 | 1.3995 |
| 0.94 | 0.9205 |
| 0.985 | 0.9715 |
| 1.27 | 1.243 |
| 1.165 | 1.131 |
| 2.605 | 2.535 |
| 1.775 | 1.681 |
| 2.52 | 2.4055 |
| 2.86 | 2.7795 |
| 2.24 | 2.136 |
| 1.64 | 1.579 |
| 3.025 | 2.971 |
| 3.09 | 3.0445 |
| 2.17 | 2.068 |
| 2.765 | 2.7335 |
| 1.57 | 1.511 |
| 2.39 | 2.319 |
| 2.055 | 1.948 |
| 0.88 | 0.869 |
| 3.465 | 3.4505 |

ASSAY EXAMPLE 6

Determining the Change of Absorbance at Different Wavelengths and Different Cystatin C Concentrations using a Beckman Lx 20 Instrument a) Reagents: see Assay Example 1
b) Procedure:
The instrument was set to mix 230 µl assay with 6 µl sample, followed by mixing of 50 µl immunoparticles to the assay mixture. The instrument was further set to measure the rate of the change of absorbance from 12 to 52 seconds after the mixing of the reagents.
The Beckman Lx20 instrument—as many other clinical spectrophotometric automated instruments—operates with a main (primary) measurement wavelength and a secondary measurement wavelength (around 700 nm), and provides results of the measurement at the main wavelength, corrected for the reading at the secondary wavelength. Two experiments were performed, one with an instrument setting with a primary measurement wavelength of 410 nm, and one experiment with an instrument setting with a primary measurement wavelength at 470 nm. For both experiments the secondary wavelength was set at 700 nm.

The following rates of change of mAbs Units/min were obtained:

| Conc. cystatin C in sample | 410 nm | 470 nm |
|---|---|---|
| 0.42 mg/l | 36.2 | 12.0 |
| 0.62 mg/l | 53.9 | 15.7 |
| 0.85 mg/ml | 81.2 | 27.3 |
| 1.69 mg/ml | 203.1 | 61.1 |
| 3.38 mg/l | 529.3 | 168.1 |
| 8.05 mg/l | 1095 | 390.8 |

The invention claimed is:

1. A turbidimetric immunoassay method for assessing human Cystatin C in a human body liquid sample comprising
   a) forming an assay mixture by contacting said sample with a nanoparticle-antibody conjugate comprising nanoparticles suitable for turbidimetric measurement, wherein said nanoparticles are coated with anti-human Cystatin C antibodies or antigen binding fragments thereof, to bind said Cystatin C, wherein said coated nanoparticles are coated with 5 to 35% of binding antibody per total weight of nanoparticle-antibody conjugate and wherein said coated nanoparticles have a median diameter in the range of 59 to 160 nm, and
   b) assessing the human Cystatin C content by measuring the change in turbidity of said mixture by determining the absorbance change at at least one wavelength in a range between above 370 nm and below 500 nm; thereby assessing human Cystatin C in a human body liquid sample.

2. The method of claim 1, wherein an initial rate of absorbance change is determined.

3. The method of claim 1, wherein an initial rate of absorbance change is determined in at least one time interval of about 5 to 300 seconds starting immediately at or shortly after forming said assay mixture.

4. The method of claim 1, wherein said antibodies are polyclonal non-human, non-rodent antibodies against human Cystatin C.

5. The method of claim 4, wherein said polyclonal antibodies are avian antibodies against human Cystatin C.

6. The method of claim 4, wherein at least 25 wt.-% of said polyclonal antibodies or fragments have been obtained by affinity purification with human Cystatin C.

7. The method of claim 1, wherein the antibodies comprise (a) monoclonal antibodies binding to a single epitope of human Cystatin C or (b) a set of two or more species of monoclonal antibodies, wherein each species of monoclonal antibodies binds a different epitope of human Cystatin C or two or more species bind identical epitopes with different binding strength.

8. The method of claim 7, wherein the monoclonal antibodies are of non-human origin.

9. The method of claim 1, wherein the coated nanoparticles have a mean diameter of more than 58 nm.

10. The method of claim 9, wherein the coated nanoparticles have a mean diameter in the range of 80 to 105 nm.

11. The method of claim 1, wherein the coated nanoparticles are coated with about 5 to 35% of binding antibody per total weight of the nanoparticle-antibody conjugate.

12. The method of claim 1, wherein the coated nanoparticles are coated with a mixture of anti-human Cystatin C antibody and at least one inert protein.

13. The method of claim 1, wherein the nanoparticles are made of polystyrene, polyvinyl chloride, epoxy resin, polyvinylidene chloride, poly-alpha-naphthyl methacrylate, polyvinylnaphthalene, and corresponding copolymers thereof.

14. The method of claim 1, wherein the turbidity change is measured via the change in the said assay mixture's absorbance of light at at least one wavelength in the range of 350 to 499 nm and at a temperature in the range of 10 to 50 degree Celsius.

15. The method according to claim 1, wherein when a correlation curve against nephelometric methods are constructed, an intercept value of less than 0.15 mg/l of Cystatin is obtained for the turbidimetric method for a corresponding value of 0 mg/l Cystatin C as obtained by the nephelometric method.

16. The method according to claim 1, wherein when a correlation curve against non-homogeneous immunoassay methods is constructed, an intercept value of less than 0.25 mg/l of Cystatin is obtained for a corresponding value of 0 mg/l Cystatin C.

17. The method according to claim 1 having an interference from 15 mmol/liter triglycerides in the sample of less than 6% on the measured value of Cystatin C at a level of 1.2 mg Cystatin C per l.

18. The method according to claim 1 having a deviation from linearity below 5% in a measurement range of 1.32 to 7.5 mg Cystatin C per liter, and a deviation from linearity below 15% in the measurement region from measurement range of 0.75 to 1.32 mg Cystatin C per liter.

19. The method according to claim 1, wherein said method determines the Cystatin C concentration of a sample by measuring an initial rate of the increase of the absorbance, (a) by direct recording at the time of the mixing, or (b) by recording shortly after the mixing combined with a backwards extrapolation to the initial increase absorbance, or (c) by measuring the absorbance difference between two or more time-points less than 5 minutes after the mixing of the sample and the reagents.

20. A method for the assessment of the glomerular filtration rate of a mammal, which method comprises the turbidimetric assessment of human Cystatin C according to claim 1 and correlating the observed Cystatin C content of said body liquid sample with the glomerular filtration rate of said mammal.

* * * * *